(12) United States Patent
MacRae et al.

(10) Patent No.: US 6,644,305 B2
(45) Date of Patent: Nov. 11, 2003

(54) NASAL INHALER

(75) Inventors: John MacRae, Carlisle (CA); Martin Foley, London (CA); Jerry Grychowski, Lake Zurich, IL (US)

(73) Assignee: Trudell Medical International, London (CA)

( * ) Notice: Subject to any disclaimer, the term of this patent is extended or adjusted under 35 U.S.C. 154(b) by 0 days.

(21) Appl. No.: 09/834,037

(22) Filed: Apr. 11, 2001

(65) Prior Publication Data

US 2002/0046751 A1 Apr. 25, 2002

Related U.S. Application Data

(60) Provisional application No. 60/197,779, filed on Apr. 14, 2000.

(51) Int. Cl.$^7$ .............................................. A61M 11/00
(52) U.S. Cl. ............................. 128/200.21; 128/200.14; 128/200.22
(58) Field of Search ....................... 128/200.24, 200.21, 128/200.14, 200.11, 200.12, 200.22, 201.18, 203.12, 203.14, 203.15, 203.21, 203.28, 205.13, 205.14, 205.24; 222/153.13, 47, 168, 257, 380, 387; 239/338; 604/94.01, 58, 257; D24/115

(56) References Cited

U.S. PATENT DOCUMENTS

| | | | | |
|---|---|---|---|---|
| 2,485,184 A | * | 10/1949 | Blackman et al. | 128/200.22 |
| 2,566,806 A | * | 9/1951 | Miller | 128/200.18 |
| 2,582,529 A | * | 1/1952 | Curry et al. | 128/200.18 |
| 2,655,918 A | * | 10/1953 | Jones | 128/200.22 |
| 2,672,141 A | * | 3/1954 | Filger | 128/200.22 |
| 4,083,368 A | * | 4/1978 | Freezer | 128/203.22 |
| 4,117,844 A | * | 10/1978 | James | 128/203.15 |
| 4,274,403 A | | 6/1981 | Struve | |
| 4,641,644 A | | 2/1987 | Andersson et al. | |
| 4,653,494 A | | 3/1987 | Ruderian | |
| 4,678,106 A | * | 7/1987 | Newell et al. | 222/162 |
| D295,787 S | | 5/1988 | Hegemann et al. | |
| 4,771,769 A | | 9/1988 | Hegemann et al. | |
| 4,860,738 A | | 8/1989 | Hegemann et al. | |
| 4,969,578 A | | 11/1990 | Gander et al. | |

(List continued on next page.)

FOREIGN PATENT DOCUMENTS

| | | |
|---|---|---|
| CA | 2 207 219 A | 12/1998 |
| DE | 195 24 033 A | 1/1997 |
| EP | 0 341 967 | 11/1989 |
| EP | 0 412 524 A1 | 2/1991 |

(List continued on next page.)

OTHER PUBLICATIONS

Mygind, N. et al., "Aerosol Distribution in the Nose," *Rhinology*, XVI, 79–88 (1978).

(List continued on next page.)

*Primary Examiner*—Weilun Lo
*Assistant Examiner*—Teena Mitchell
(74) *Attorney, Agent, or Firm*—Brinks Hofer Gilson & Lione

(57) ABSTRACT

A nasal inhaler for introducing a substance to a nasal cavity of a user. The nasal inhaler comprises a chamber having an interior and an exterior, an outlet comprising an air exit passageway in flow communication with the interior of the chamber, a one-way air inlet valve in one-way flow communication with the interior of the chamber, and a dosage inlet passageway in flow communication with the interior of the chamber. A container includes a dispensing portion disposed in the dosage inlet passageway. In preferred embodiment, an adapter defines the dosage inlet passageway and is connected to the chamber. A mask also can be connected to the outlet. A method for dispensing a substance into the nasal cavity of the user comprises inserting the outlet into the nasal cavity, dispensing the substance into the chamber and inhaling through the outlet. A method for assembling a nasal inhaler assembly also is provided.

41 Claims, 25 Drawing Sheets

U.S. PATENT DOCUMENTS

| | | | | |
|---|---|---|---|---|
| 5,020,527 A | * | 6/1991 | Dessertine | 128/200.23 |
| 5,064,122 A | | 11/1991 | Kamishita et al. | |
| 5,224,471 A | * | 7/1993 | Marelli et al. | 128/200.14 |
| 5,437,267 A | | 8/1995 | Weinstein et al. | |
| 5,487,378 A | | 1/1996 | Robertson et al. | |
| 5,505,193 A | | 4/1996 | Ballini et al. | |
| 5,702,362 A | | 12/1997 | Herold et al. | |
| 5,797,390 A | | 8/1998 | McSoley | |
| 5,899,202 A | * | 5/1999 | Ohki et al. | 128/203.15 |
| 5,901,703 A | * | 5/1999 | Ohki et al. | 128/200.14 |
| 5,983,893 A | | 11/1999 | Wetterlin et al. | |
| 5,989,217 A | * | 11/1999 | Ohki et al. | 128/200.22 |
| 6,065,471 A | * | 5/2000 | Schaeffer et al. | 128/203.15 |
| 6,116,239 A | | 9/2000 | Volgyesi | |
| 6,186,141 B1 | * | 2/2001 | Pike et al. | 128/203.12 |
| 6,223,744 B1 | * | 5/2001 | Garon | 128/200.14 |
| 6,273,084 B1 | * | 8/2001 | Frid | 128/200.23 |
| 6,302,101 B1 | | 10/2001 | Py | |
| 6,352,181 B1 | * | 3/2002 | Eberhard et al. | 222/153.13 |
| 6,363,932 B1 | * | 4/2002 | Forchione et al. | 128/200.14 |
| 6,364,166 B1 | * | 4/2002 | Ritsche et al. | 222/153.13 |
| 6,418,924 B1 | * | 7/2002 | Poley et al. | 128/200.14 |
| 6,435,179 B1 | * | 8/2002 | Kolbel | 128/203.12 |
| 6,510,847 B1 | * | 1/2003 | Helgesson et al. | 128/200.14 |
| 2002/0008122 A1 | | 1/2002 | Ritsche et al. | |
| 2002/0017294 A1 | | 2/2002 | Py | |

FOREIGN PATENT DOCUMENTS

| | | |
|---|---|---|
| EP | 0 526 824 A2 | 2/1993 |
| EP | 0 412 524 B1 | 3/1993 |
| EP | 0 563 120 B1 | 10/1993 |
| EP | 0 563 131 B1 | 10/1993 |
| EP | 0 438 531 B1 | 1/1994 |
| EP | 0 617 629 B1 | 10/1994 |
| EP | 0 652 021 B1 | 5/1995 |
| EP | 0 683 648 B1 | 11/1995 |
| GB | 691 548 | 5/1953 |
| GB | 834 137 | 5/1960 |
| GB | 975 754 | 11/1964 |
| WO | WO 96/16687 | 6/1996 |

OTHER PUBLICATIONS

Soderberg–Warner, Margaret, L., "Nasal Septal Perforation associated with Topical Corticosteroid Therapy," *The Journal of Pediactrics*, 105, 5, 840–841 (1984).

Newman, S.P. et al., Deposition Pattern From a Nasal Pump Spray, *Rhinology*, 25, 77–82 (1987).

Mygind, N. et al., "Topical Corticosteroid Therapy of Rhinitis," *Clin. Immunother.*, 5, 122–136 (1996).

Hjuler, Pederson, W. et al., "Nasal Inhalation of Budesonide From a Spacer in Children with Perennial Rhinitis and Asthma," *Allergy*, 53, 383–387 (1998).

Pedersen, B. et al., "Nasal Inhalation of the Glucocorticoid Budesonide From a Spacer for the Treatment of Patients with Pollen Rhinitis and Asthma," *Allergy*, 45, 451–456 (1990).

Mygind, N. et al., "Simultaneous Treatment of Rhinitis and Asthma by Nasal Inhalation of Corticosteroid From a Spacer," *Allergy*, 54, 132–135 (1999).

Henriksen, J.M., et al., "Effect of an Intranasally Administered Corticosteroid (Budesonide) on Nasal Obstruction, Mouth Breathing, and Asthma".

International Search Report, PCT/IB01/0617.

* cited by examiner

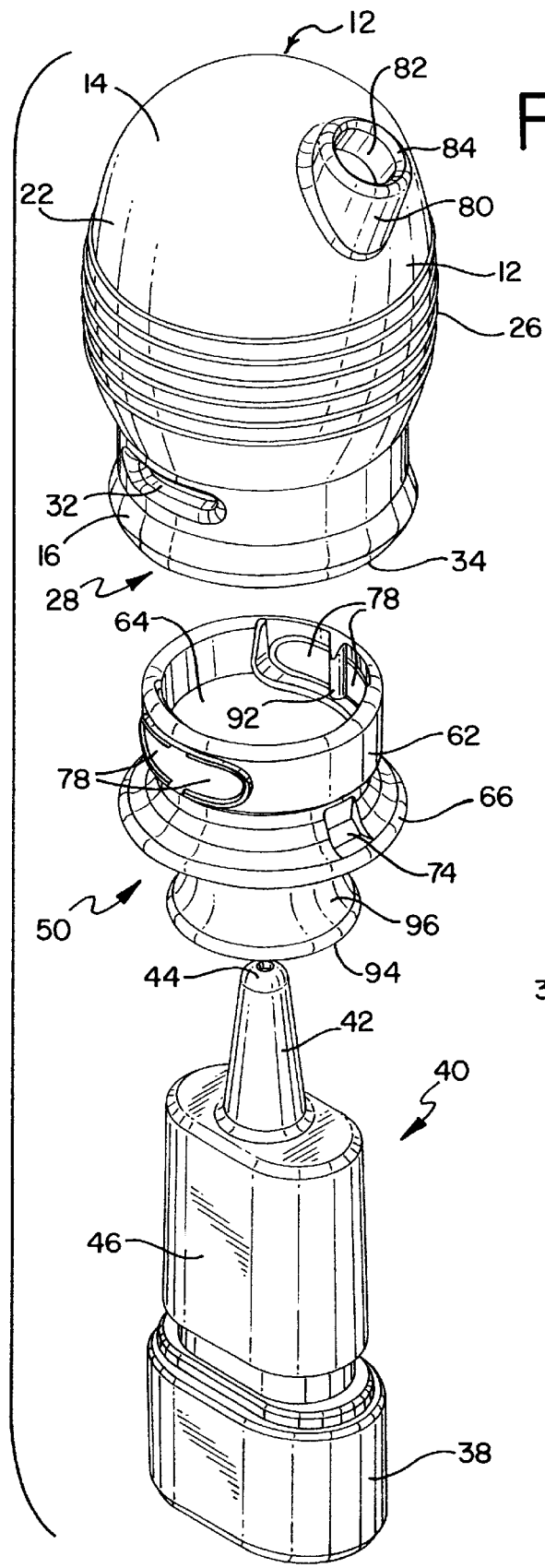
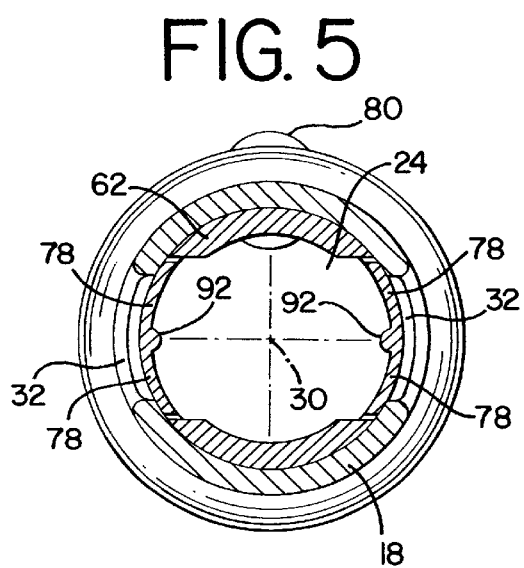
FIG. 6
FIG. 5

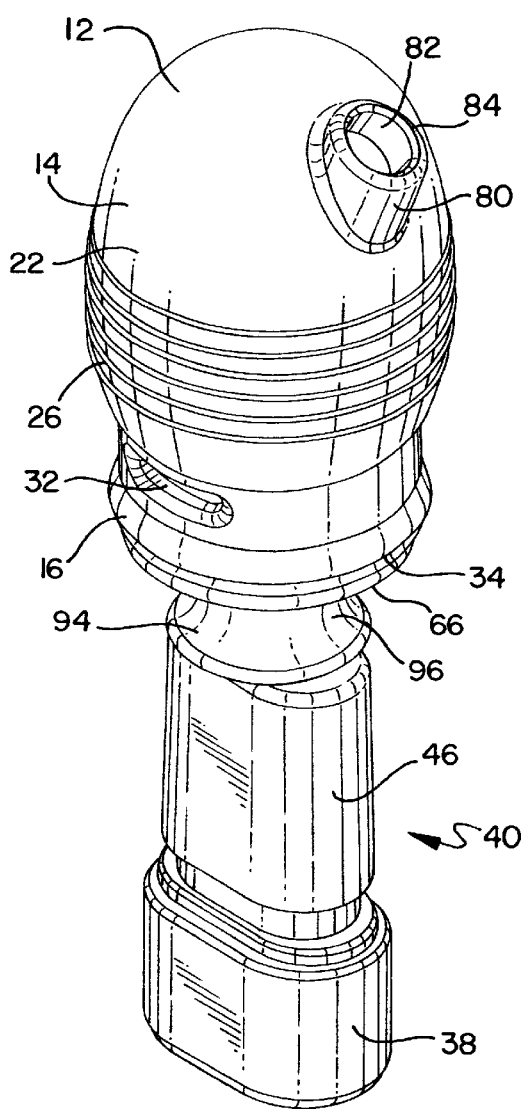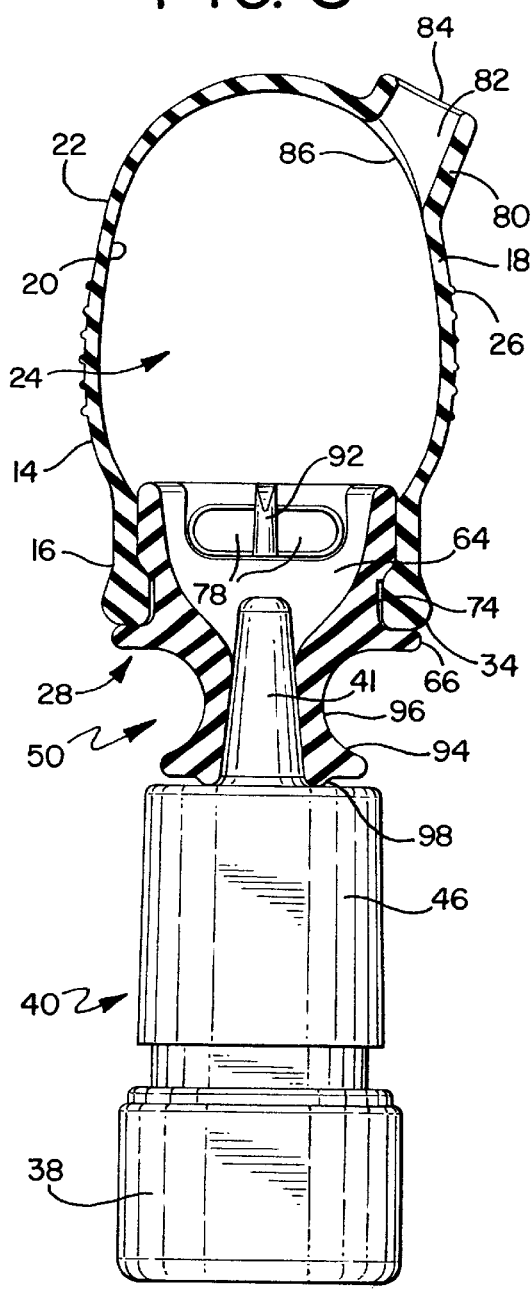

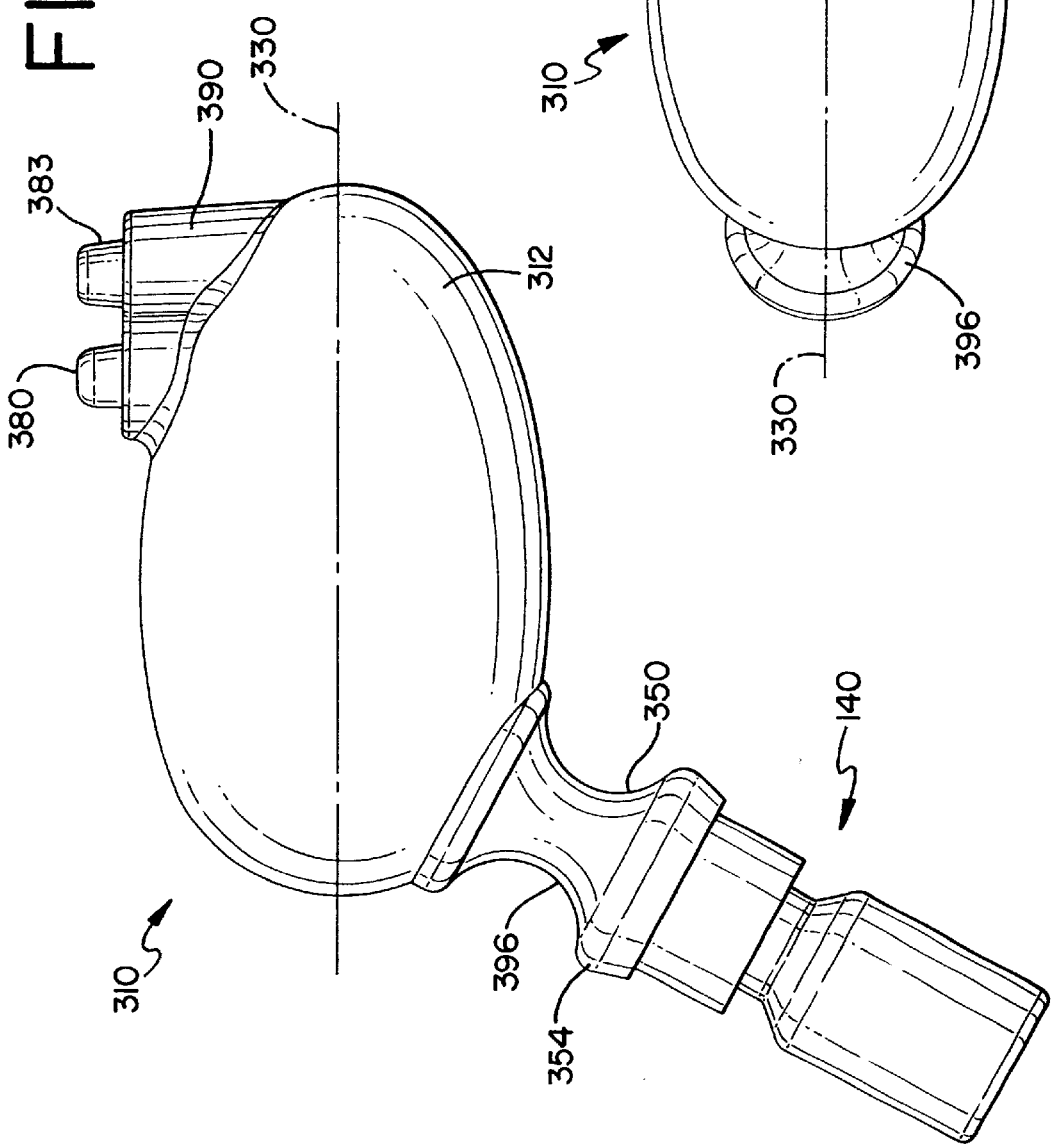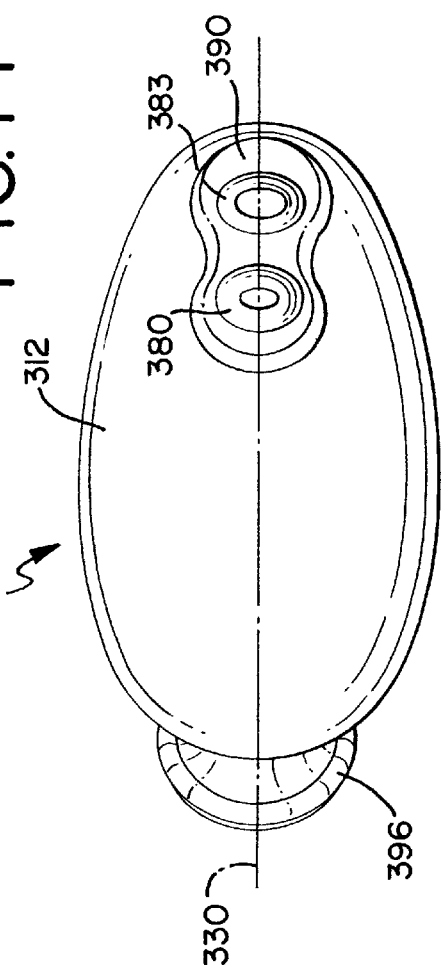

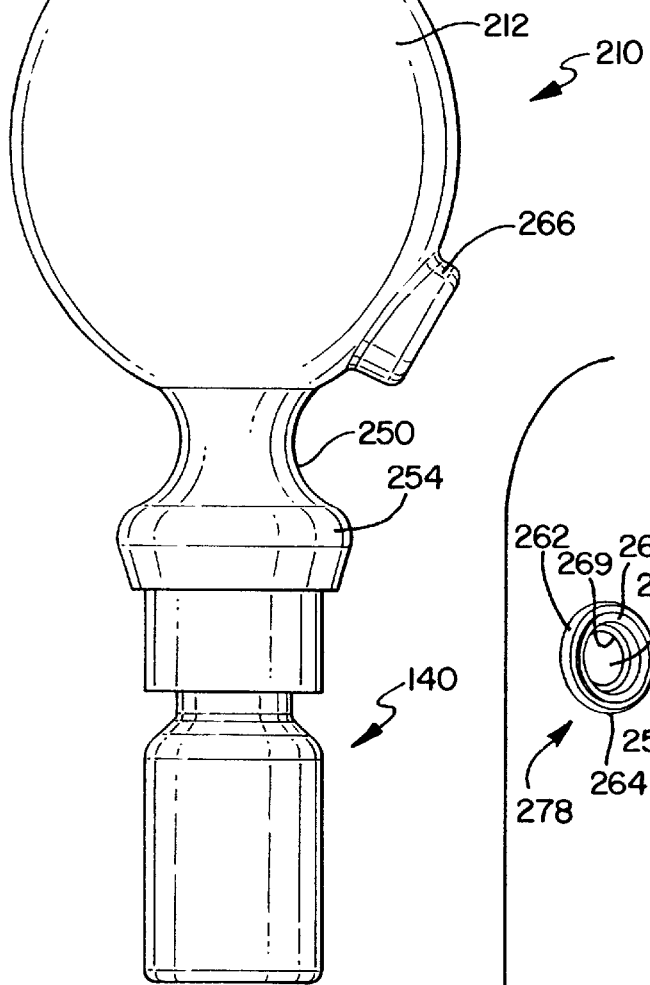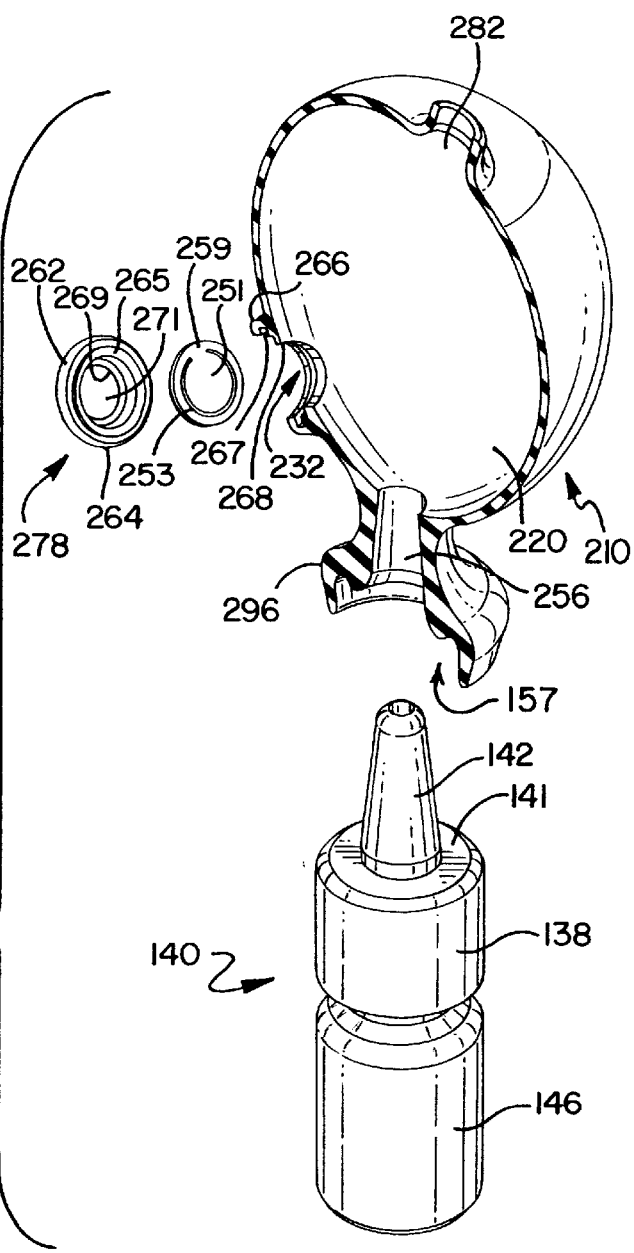

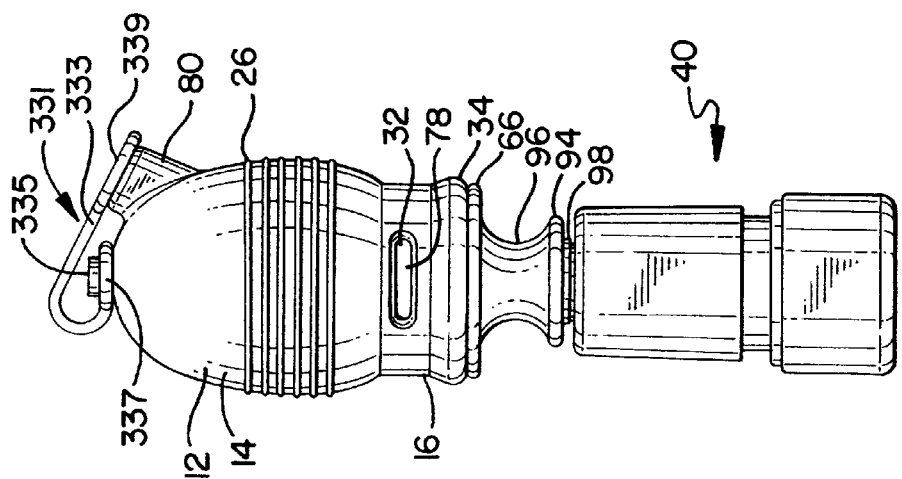
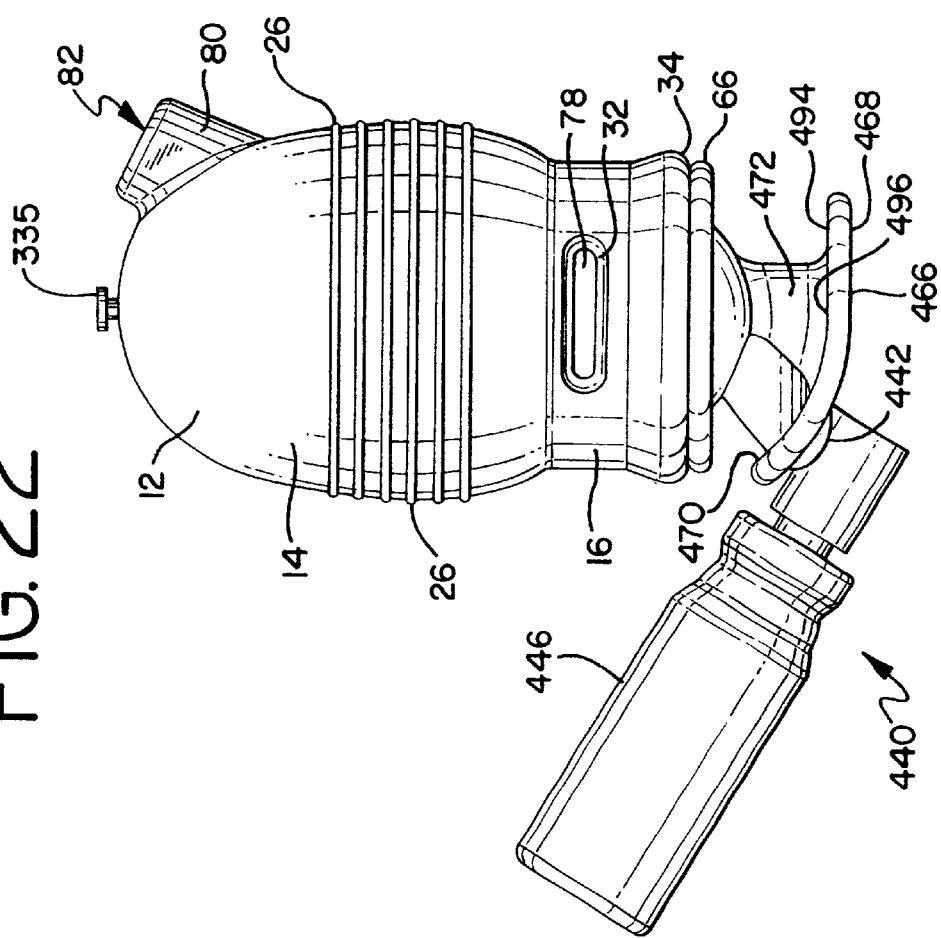

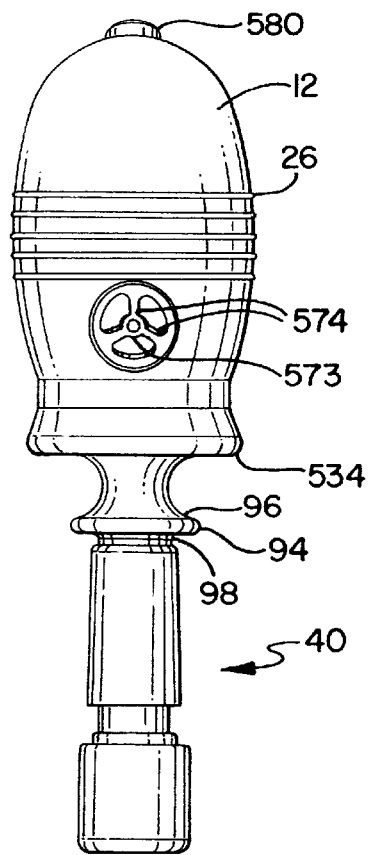
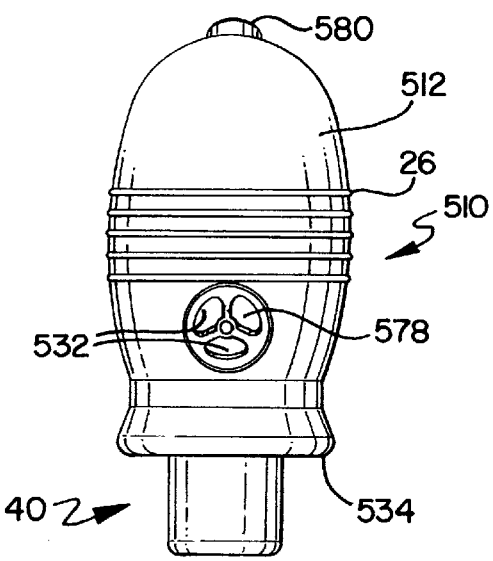
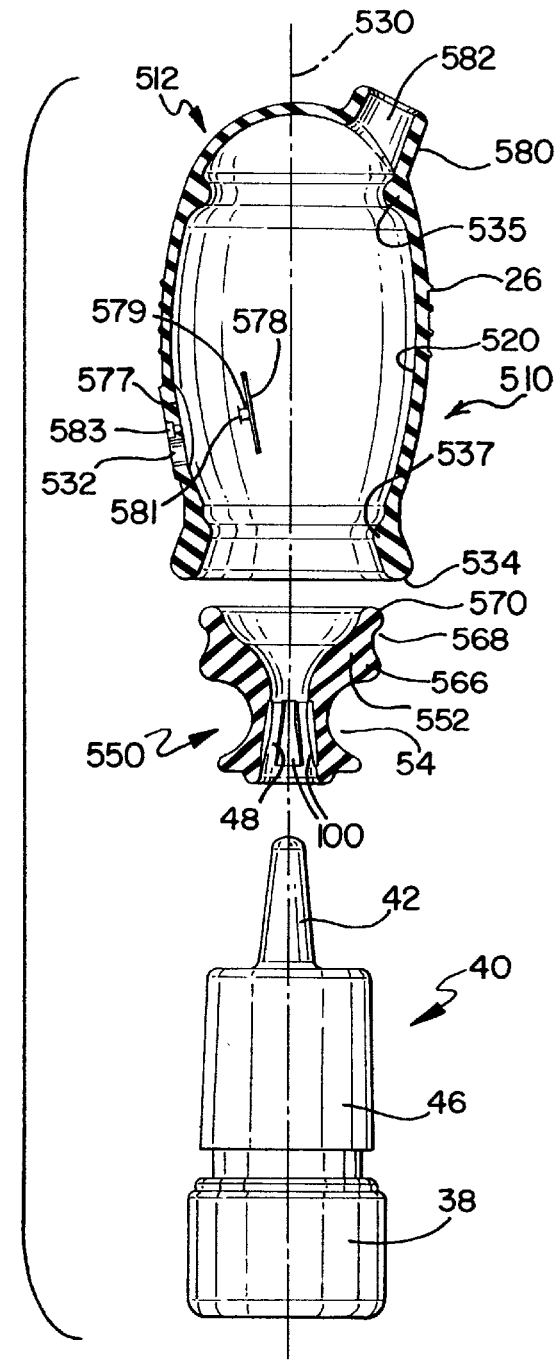

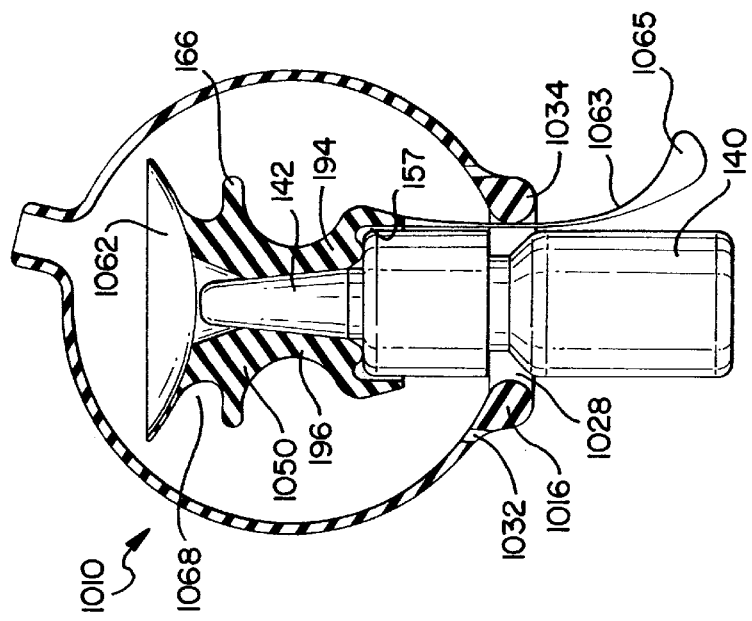
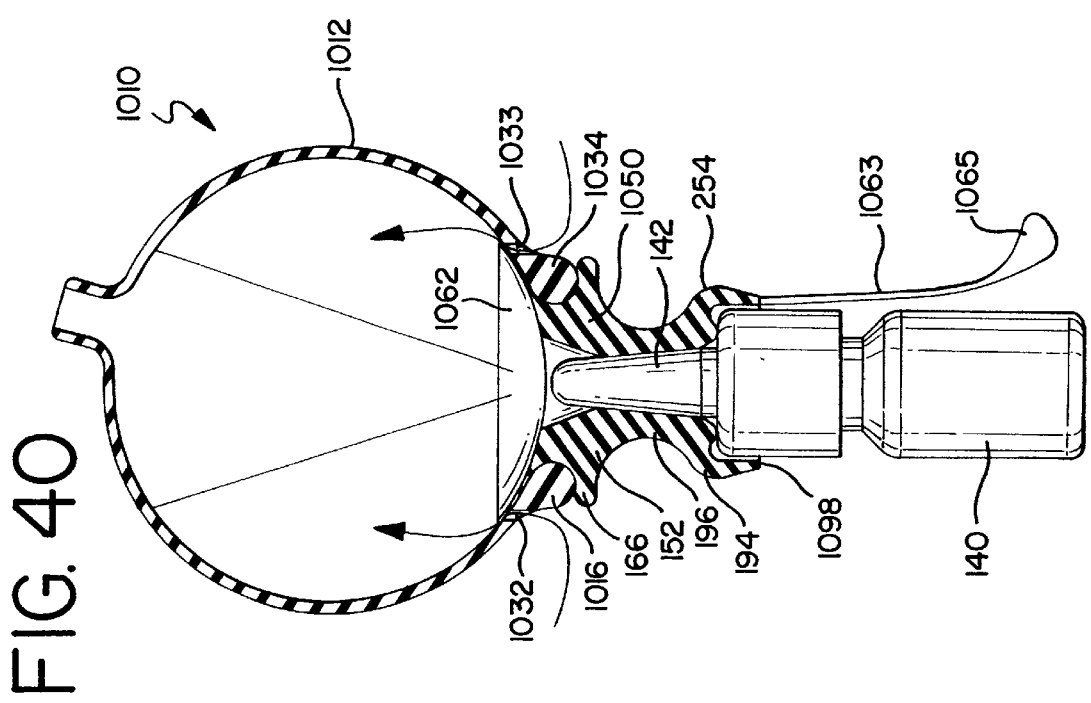

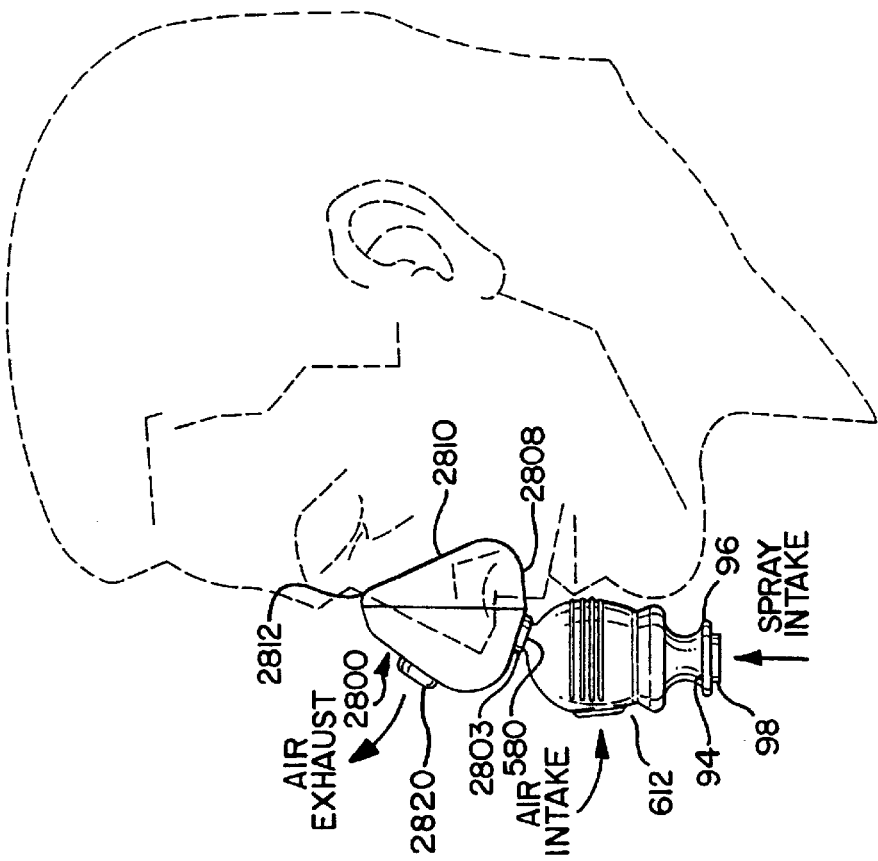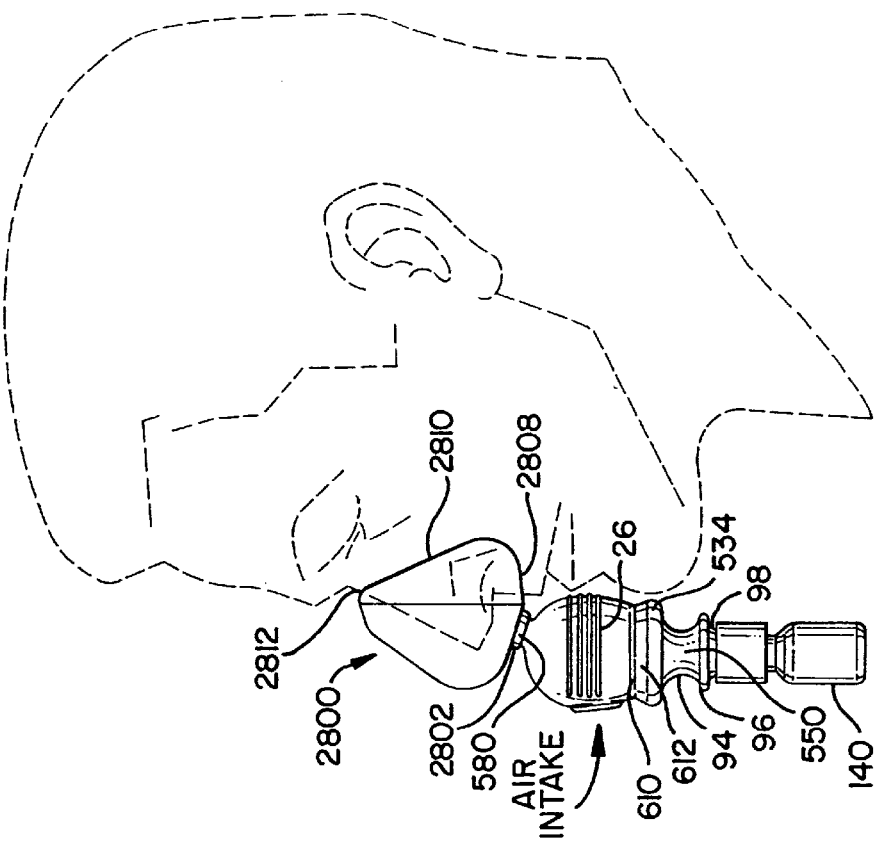

NASAL INHALER

This application claims the benefit of U.S. Provisional Application S/N 60/197,779, filed Apr. 14, 2000, the entire disclosure of which is hereby incorporated herein by reference.

BACKGROUND

The invention relates generally to nasal inhalers, and in particular, to a nasal inhaler suited for use with a nasal delivery device for the administration of a medication or other substance to the nasal cavity of a user.

The nose can be an important route for the delivery of various substances aimed at treating various ailments. For example, the nose, including its various nasal membranes, cavities and passageways, traditionally has been used as a route for the delivery of substances aimed at treating upper respiratory ailments, such as sinusitis, allergic conditions, reactive airway diseases, and rhinitis. Rhinitis is one of the more prevalent respiratory ailments and is characterized by the primary symptoms of sneezing, itching, and nasal obstruction. Substances commonly used to treat upper respiratory ailments such as rhinitis include anti-cholinergic agents, adrenegically acting decongestants, topical buffering compounds, and corticosteroid anti-inflammatory agents.

More recently, the nose also has served as a route for the delivery of various substances aimed at treating non-respiratory ailments, including, for example, migraines, diabetes, convulsions, anaphylaxis, anxiety, Parkinson's disease, and erectile dysfunction. Substances used to treat these types of ailments can include, for example, pain medications and insulin.

Most of the substances delivered to a user through their nose, and in particular to the user's nasal membranes, are delivered in aerosol or aqueous form through nasal delivery devices, including pressurized metered dose nasal inhalers, nasal spray containers, and dry powder inhalers. In order to ensure a positive therapeutic effect, substances delivered to the nose to treat the above noted ailments are preferably delivered to the area of the nose having a rich blood vessel plexus. This area of the nose typically is found on the lateral sidewall to the interior of the nose, and encompasses the squamous epithelisum prior to the transitional region to the nasal turbinates.

When delivering various substances to the nasal membranes, nasal delivery devices can cause irritation, infection, bleeding, and variable absorption. Most of these symptoms result from one or more disadvantages associated with such devices. For example, pressurized metered dose nasal inhalers often dispense aerosol particles at a high exit velocity, which can result in considerable pain to the user and may result in bleeding and infection. In addition, because of the pain associated with such velocities, users may have a tendency of aiming the outlet straight into the nasal cavity, instead of towards the interior lateral sidewall of the nose. In addition to pain, the high exit velocity of the particles may result in a narrow proximal deposition of the substance on the nasal membranes. Moreover, in many cases, the substance will be delivered on the nasal septum. Repeated delivery to the nasal septum can result in damage to the septum, including, for example, a perforation of the septum.

Alternatively, spray containers generally dispense the particles of substance at a lower exit velocity. However, the particle size is relatively large resulting in a large portion of the delivered substance coming back out of the nose and/or ending up at the back of throat, eventually making its way down to the stomach. This can result in a wastage of the substance, and can decrease the overall therapeutic effect on the user.

SUMMARY

Briefly stated, one aspect of the invention is directed to a nasal inhaler for introducing a substance to the nasal cavity of a user. The nasal inhaler preferably comprises a chamber having an interior and an exterior. In a preferred embodiment, the chamber is flexible. An outlet comprises an exit passageway that is in flow communication with the interior of the chamber. The outlet is preferably shaped to be received in the nasal vestibule of the user. In a preferred embodiment, a single outlet is in communication with the interior. In an alternative embodiment, the nasal inhaler includes a pair of outlets spaced and configured to be received in both of the nasal vestibules of the user. A one-way air inlet valve is in one-way flow communication with the interior of the chamber at a location spaced from the exit passageway. The one-way valve is operative to permit one-way flow of air from the exterior to the interior of the chamber. A dosage inlet passageway is in flow communication with the interior of the chamber at a location spaced from the exit passageway and from the one-way valve. Preferably, the dosage inlet passageway and the exit passageway define axes that are not coaxial.

In a preferred embodiment of the invention, an adapter defines the dosage inlet passageway and is connected to the chamber. Preferably, the adapter comprises a handle having a grippable portion. In a preferred embodiment, the adapter is releasably connected to the chamber with a detent. Preferably, the detent comprises a combination of a rib and groove formed on one or the other of the chamber and the adapter. In an alternative embodiment, the adapter and the chamber are integrally formed.

In another aspect, the adapter is moveably connected with the chamber. The adapter is moveable between a retracted position, wherein at least a portion of the adapter is disposed in the interior of the chamber, and an extended position, wherein at least a portion of the adapter extends from the chamber. In one embodiment, an entirety of the adapter is disposed in the interior of the chamber when the adapter is in the retracted position. In other embodiments, at least a portion of the adapter extends from the chamber when the adapter is in the retracted position. Preferably, the adapter is releasably engaged with the chamber when in the retracted and extended positions so as to prevent axial movement therebetween.

In yet another aspect, a nose plug extends from the exterior of the chamber adjacent the outlet. The nose plug is shaped to be received in the nasal vestibule of the user. In one embodiment, the nasal inhaler includes a pair of nose plugs positioned on opposite sides of the outlet.

In a preferred embodiment, the one-way valve is formed by a valve opening formed in the chamber and a flexible valve member overlying said valve opening. In an exemplary embodiment, the flexible valve member is formed by a flexible portion of the adapter, which covers or overlies a valve opening formed in the chamber. In another exemplary embodiment, the valve member is separate from the adapter and overlies a valve opening formed in the chamber.

In another aspect of the invention, a method for dispensing a substance into the nasal cavity of a user is provided. The method includes providing a container that holds a substance and which comprises a dispensing portion. The dispensing portion is disposed in the dosage inlet passageway. The outlet is inserted into a nasal cavity, and the substance is dispensed into the chamber. In a preferred embodiment, the user inhales through the outlet so as to draw the substance through the outlet and into the nasal cavity. At the same time, air is drawn into the chamber through the one-way valve. In a preferred embodiment, the user can further compress the chamber to force the substance through the outlet. Preferably, the substance is dispensed into the chamber at a first velocity and is drawn into the nasal cavity through the outlet at a second velocity, wherein the second velocity is less than the first velocity. In alternative embodiments, the substance is forced out of the chamber through the exit passageway and into the nasal cavities without inhalation by the user. For example, the substance can be dispensed solely by compression of the chamber or as a result of the substance being forced into the chamber, for example, by way of a pressurized metered dose nasal inhaler.

In yet another aspect, a method of assembling a nasal inhaler assembly is provided. Preferably, the method comprises connecting an insert portion of an adapter with an intake portion of the chamber, such that the dosage inlet passageway is in flow communication with the interior of the chamber. The dispensing portion of the container is then disposed in the dosage inlet passageway. In one embodiment, a first adapter can be disconnected from the chamber, and a second adapter can thereafter be connected to the chamber.

In yet another aspect, a mask is connected to the outlet extending from the chamber. The mask can be disposed over the nose of the user so as to allow the substance to be dispensed to the user via the mask.

The present invention provides significant advantages over other nasal inhalers, nasal delivery devices, and combinations thereof. In particular, the chamber, and the configuration of the outlet and the dosage inlet passageway, allows for the substance to be introduced into the chamber at one velocity, and thereafter dispensed to the user at a second, lesser velocity. In this way, any discomfort to the user caused by the impaction of the substance on the user's nasal membranes can be reduced. At the same time, due to the associated decrease in pain experienced by the user, the user may be less likely to direct the outlet straight into the nasal vestibule, rather than towards the preferred lateral side wall of the nose. In addition, the substance is more evenly distributed in the nasal cavity, and the likelihood of a perforation of the septum can be reduced. At the same time, the substance is entrained in an aerosol form in the chamber, whereinafter it can be dispensed to the user in a more controlled and evenly distributed manner. For example, the velocity of the substance can be reduced to approximate the rate of inhalation, which allows the substance to be more evenly distributed over the target area.

In addition, a chamber made of a flexible material can be compressed or squeezed to facilitate the dispensing of the substance from the chamber through the outlet. This can be particularly helpful when the user has decreased lung capacity, or is experiencing nasal blockage, both of which can prevent inhalation through the nasal passageways. At the same time, the one-way valve prevents air from being pushed out of the chamber through the valve, thereby forcing the air through the air exit passageway.

A separate adapter also provides various advantages. For example, a single chamber can be used with different types of adapters that are configured to mate with various types of containers, including, for example, various spray containers, pressurized metered dose inhalers, and dry powder nasal inhalers. Conversely, a single container can be used with different types of adapters that are configured to mate with various chamber configurations. In either case, the detent or snap-fit coupling between the adapter and chamber allows for quick and easy assembly and disassembly of the nasal inhaler. Likewise, the releasable connection between the container and the adapter allows for easy assembly and disassembly.

Moreover, in certain embodiments, the adapter can be moveably retracted into the chamber for ease of storage and enhanced transportability. The adapter, when configured with a handle, also can facilitate the dispensing of the substance from the container, as the user can grip the handle and container and effect an actuation by moving at least one of the container or adapter toward the other.

The present invention, together with further objects and advantages, will be best understood by reference to the following detailed description taken in conjunction with the accompanying drawings.

BRIEF DESCRIPTION OF THE DRAWINGS

FIG. 5 is a cross-sectional view of the nasal inhaler taken along line 5—5 in FIG. 1.

FIG. 6 is an exploded perspective view of a nasal inhaler and a container.

FIG. 7 is a top perspective view of a nasal inhaler and a container.

FIG. 8 is a side view of a nasal inhaler and container, with the nasal inhaler shown in cross-section.

FIG. 13 is a side view of an alternative embodiment of a nasal inhaler with a container.

FIG. 14 is a top view of the nasal inhaler shown in FIG. 13.

FIG. 15 is a side view of an alternative embodiment of a nasal inhaler and a container.

FIG. 16 is an exploded perspective view of the nasal inhaler shown in FIG. 15 and a container, with the nasal inhaler shown in partial cross-section.

FIG. 22 is a side view of a nasal inhaler with an alternative embodiment of a container.

FIG. 23 is a side view of an alternative embodiment of nasal inhaler with an outlet plug in a closed position.

FIG. 24 is a rear view of an alternative embodiment of a nasal inhaler and a container, with the adapter in an extended position.

FIG. 25 is a rear view of the nasal inhaler and container shown in FIG. 24, with the adapter in a retracted position.

FIG. 26 is an enlarged side view of the nasal inhaler and container shown in FIG. 25, with the adapter in the extended position, and with the nasal inhaler shown in cross-section.

FIG. 40 is a partial cross-sectional side view of an alternative embodiment of a nasal inhaler with an adapter and a container in an extended position.

FIG. 41 is a partial cross-sectional side view of the nasal inhaler shown in FIG. 40 with the adapter and container in a retracted position.

FIG. 48 is a side view of a nasal inhaler with a container and a mask disposed over the nose of a user.

FIG. 49 is a side view of a nasal inhaler with an alternative embodiment of a mask disposed over the nose of a user.

DETAILED DESCRIPTION OF THE PRESENTLY PREFERRED EMBODIMENTS

Figure 4:
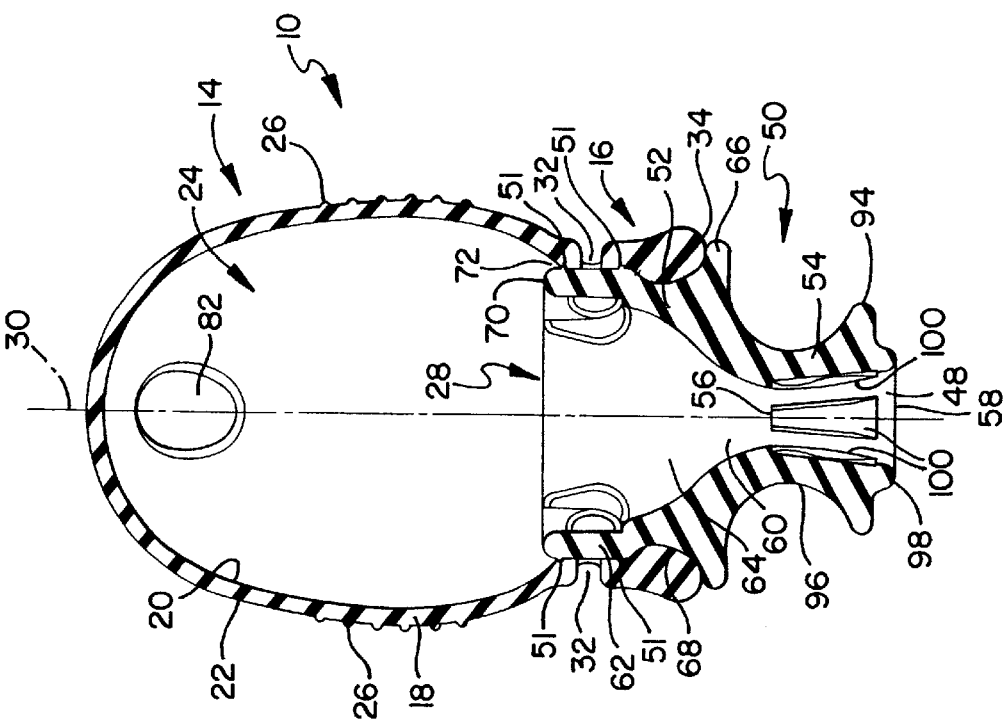
FIG. 4 is a cross-sectional view of the nasal inhaler taken along line 4—4 in FIG. 1.
Figure 1:
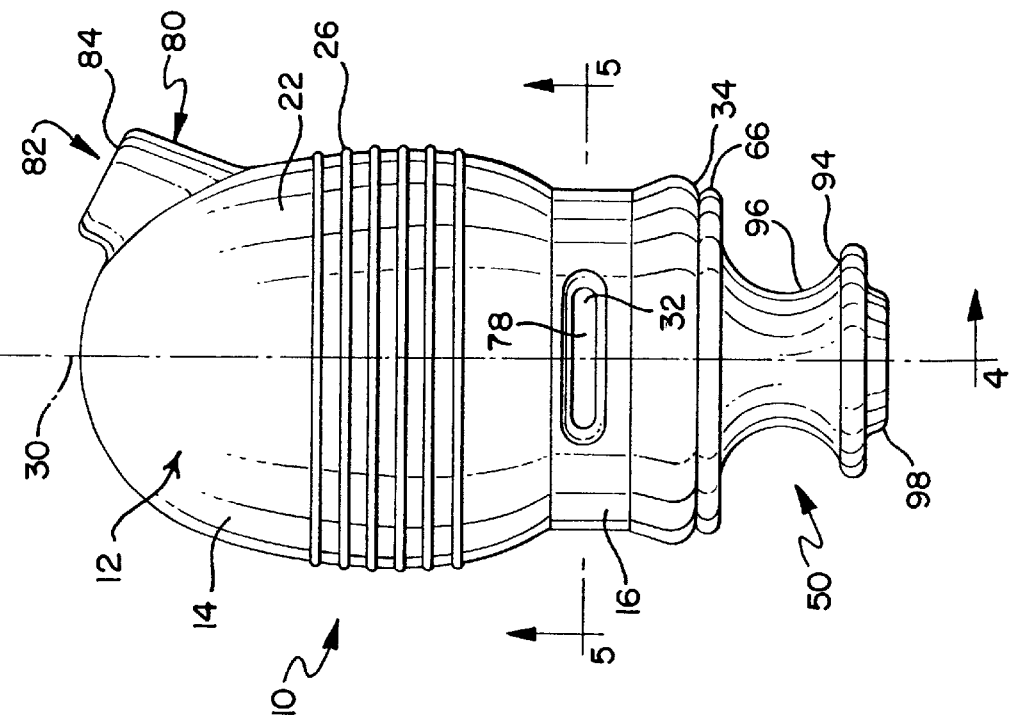
FIG. 1 is a side view of the nasal inhaler.
Figure 3:
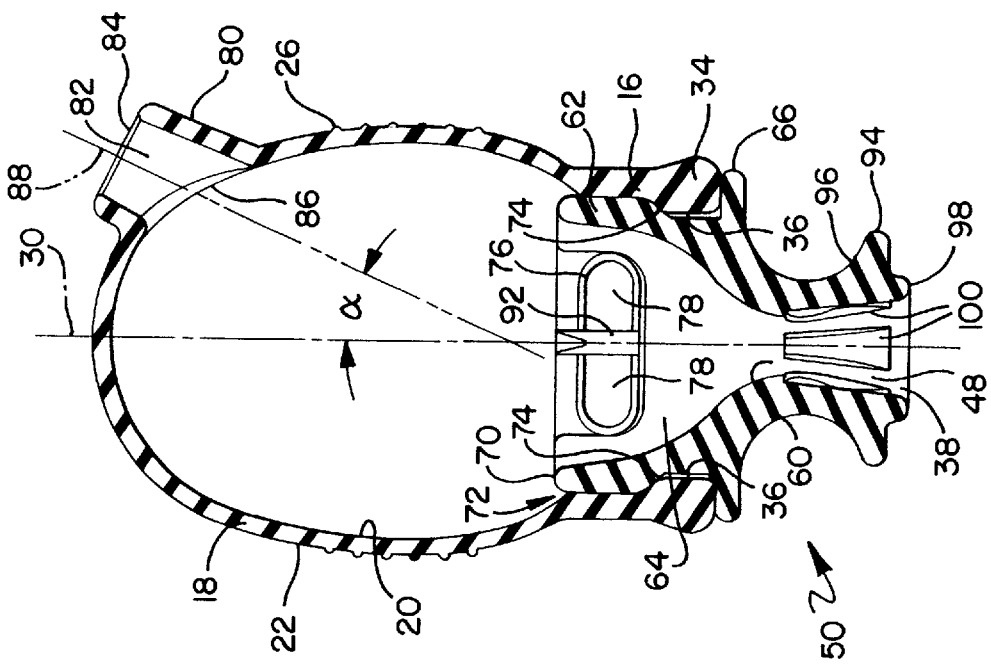
FIG. 3 is a cross-sectional view of the nasal inhaler taken along line 3—3 in FIG. 2.
Figure 2:
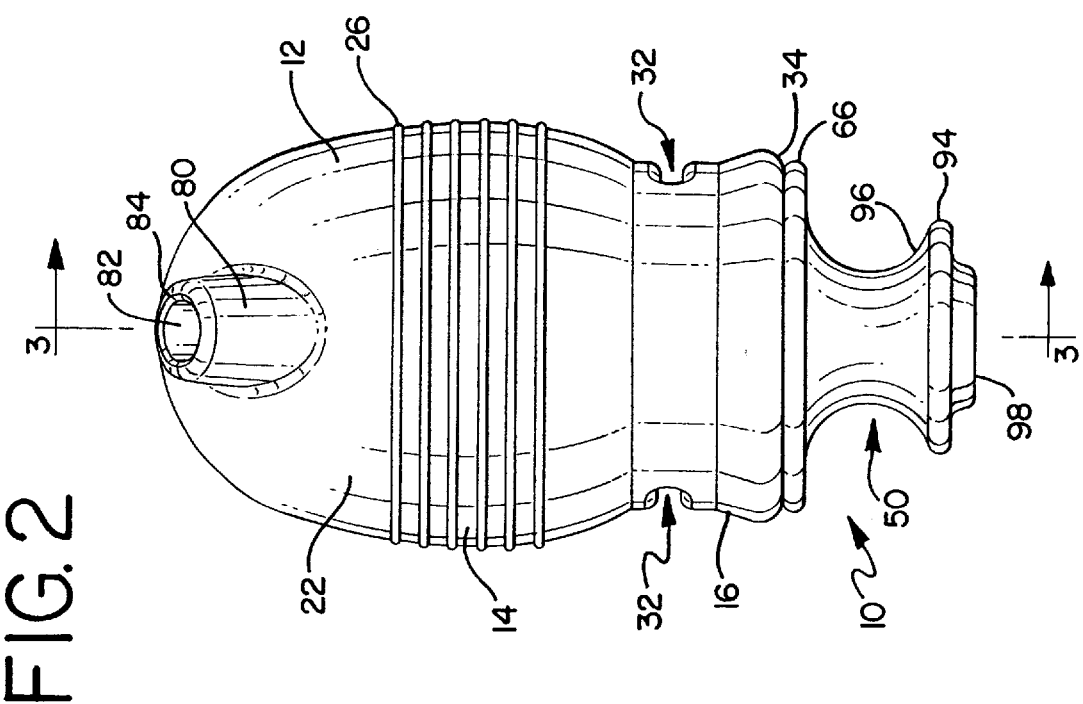
FIG. 2 is a front view of the nasal inhaler shown in FIG. 1.
Figure 9:
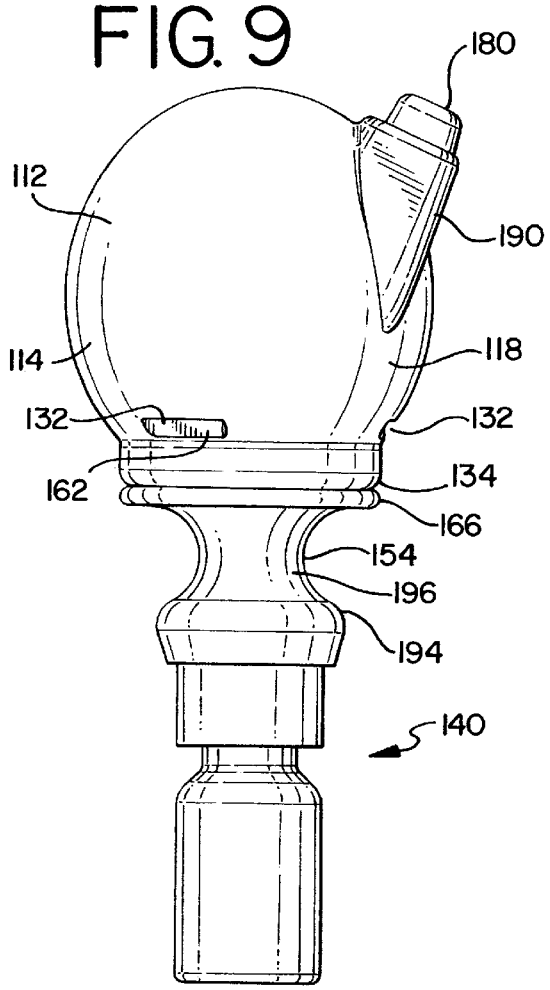
FIG. 9 is a side view of an alternative embodiment of a nasal inhaler and of a container.
Figure 10:
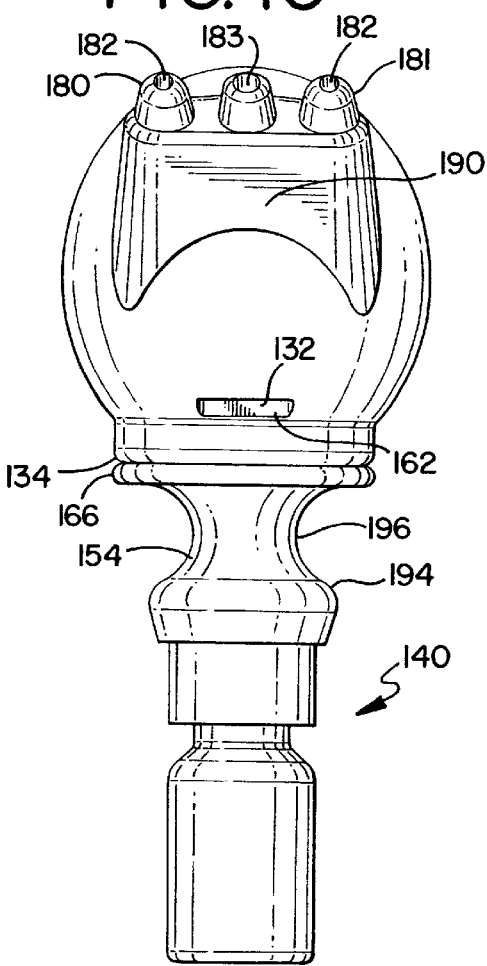
FIG. 10 is a front view of the nasal inhaler and container shown in FIG. 9.

Referring to the drawings, and in particular FIGS. 1–8, a first embodiment of a nasal inhaler 10 is shown as including a chamber 12 and an adapter 50. The chamber 12 preferably comprises a wall 18 having an interior and exterior surface. The wall 18 forms a holding portion 14 and a base portion 16. The chamber has an interior volume 24 formed by the wall 18.

Preferably, the holding portion 14 is egg shaped, and has an oval exterior contour, although other shapes would also work, including for example a spherical shape. The shape of the chamber has an aesthetically pleasing appearance and fits well in the hand of a user. Preferably, the holding portion 14 includes a plurality of axially spaced ribs 26 formed circumferentially around a periphery of the exterior surface 22 so as to provide a grippable surface for the user. Alternatively, the exterior surface 22 can be abrasive or can be provided with other raised surfaces, such as knurled surface, to enhance the grippability of the chamber 12.

The base portion 16 is preferably configured as an intake portion, which includes an intake opening 28 preferably having a circular cross-section. The intake opening 28 defines a longitudinal axis 30 extending substantially perpendicular to the cross-section. The base portion 16 also includes a pair of elongated valve openings 32 formed on opposite sides thereof. A lower edge or rim 34 of the base portion is enlarged to form a rib, or detent. In addition, a pair of tabs 36, or protuberances, extend radially inward from opposite sides of inner circumference of the lower edge or rim 34. The base can have a frusto-conically shaped interior so as to facilitate the insertion of various adapters, as described in more detail below.

Figure 38:
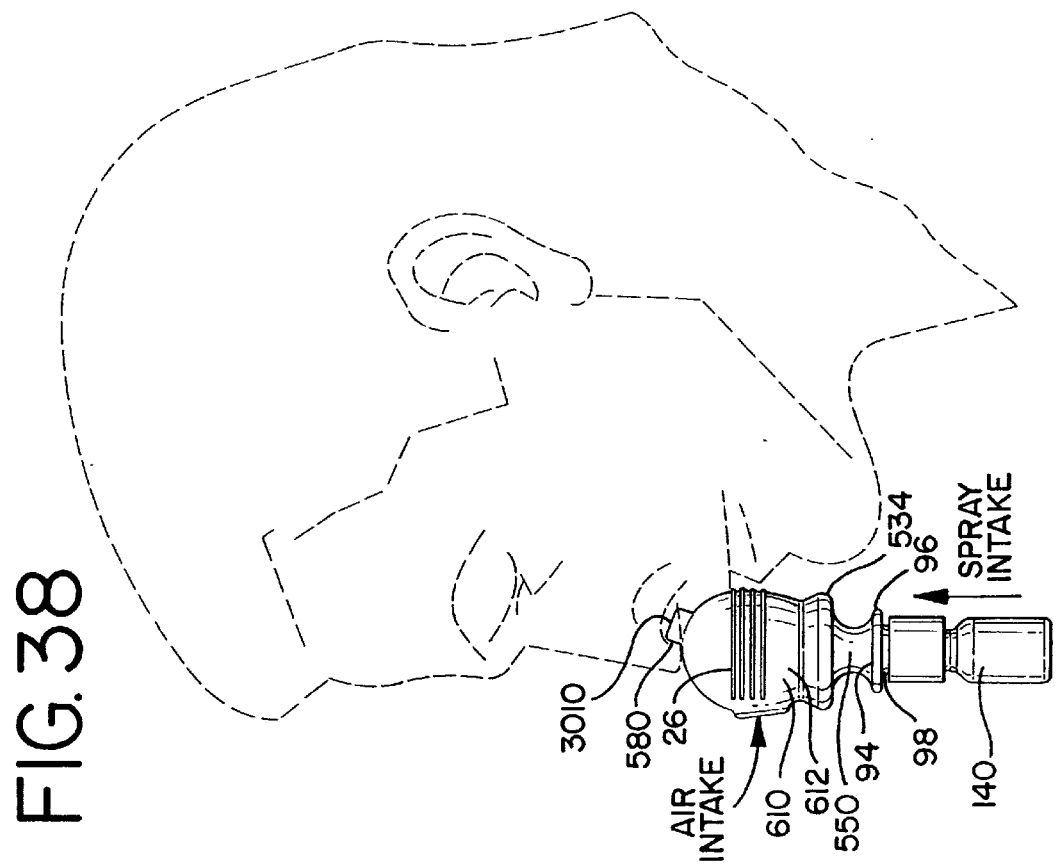
FIG. 38 is a side view of a nasal inhaler inserted into the nasal cavity of a user.
Figure 42:
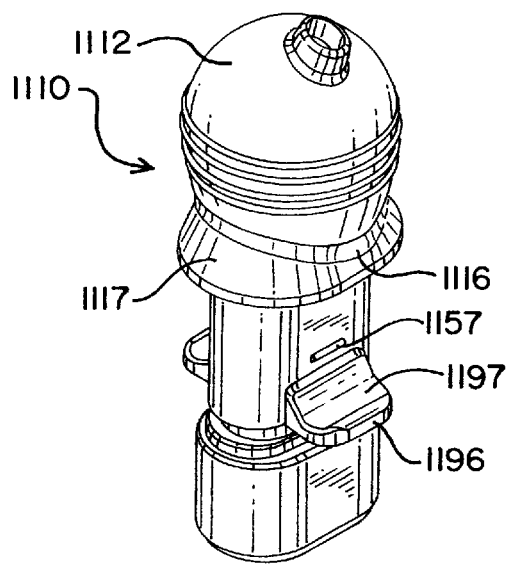
FIG. 42 is a front perspective view of an alternative embodiment of a nasal inhaler with an adapter and a container in an extended position.
Figure 43:
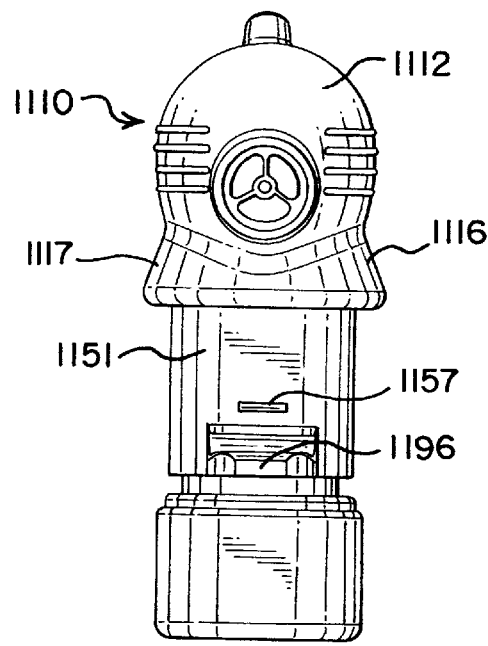
FIG. 43 is a rear view of the nasal inhaler and container shown in FIG. 42.
Figure 44:
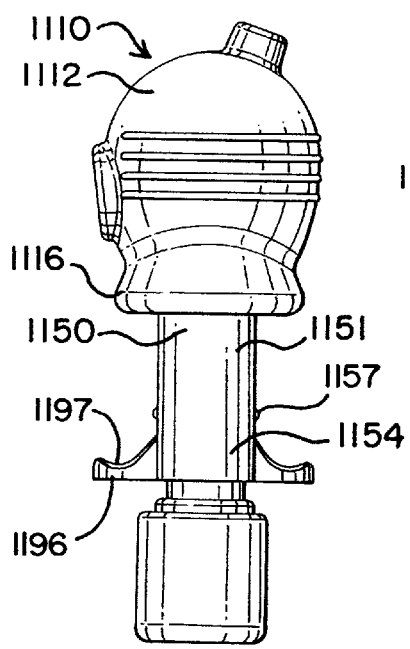
FIG. 44 is a side view of the nasal inhaler and container shown in FIG. 42.
Figure 45:
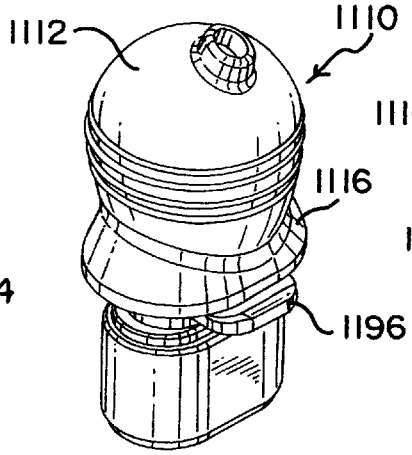
FIG. 45 is a perspective view of the nasal inhaler and container shown in FIG. 42 with the adapter and container in a retracted position.
Figure 46:
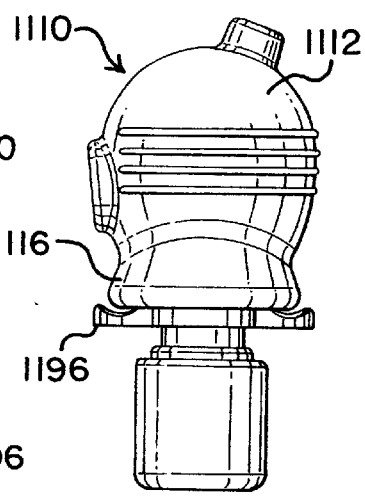
FIG. 46 is a side view of the nasal inhaler and container shown in FIG. 45.
Figure 47:
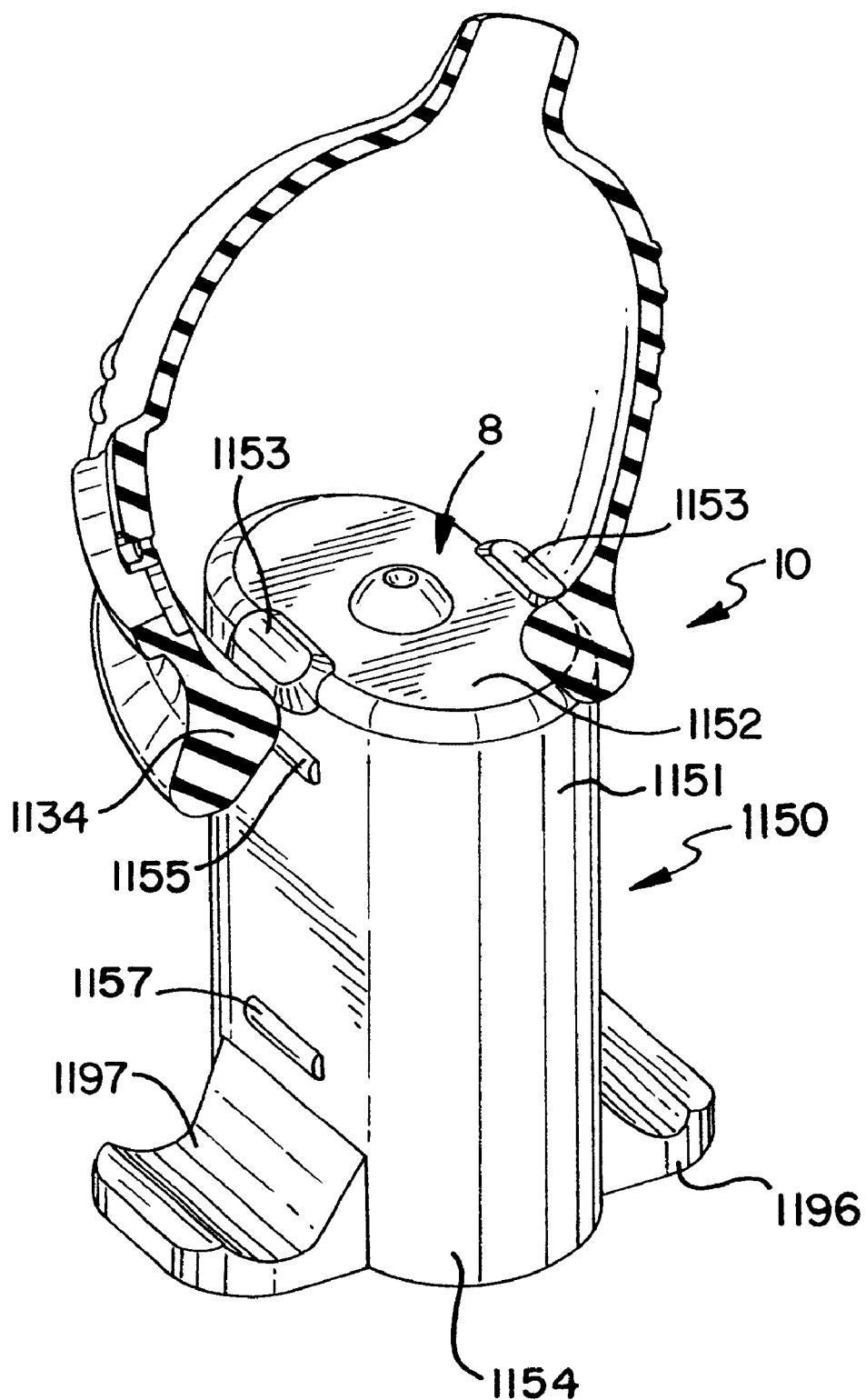
FIG. 47 is a partial cross-sectional rear perspective view of the nasal inhaler shown in FIG. 42.
Figure 50:
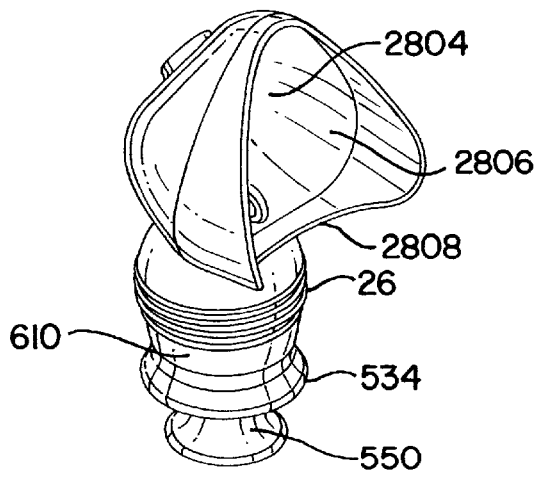
FIG. 50 is a perspective view of the nasal inhaler and mask shown in FIG. 49.
Figure 51:
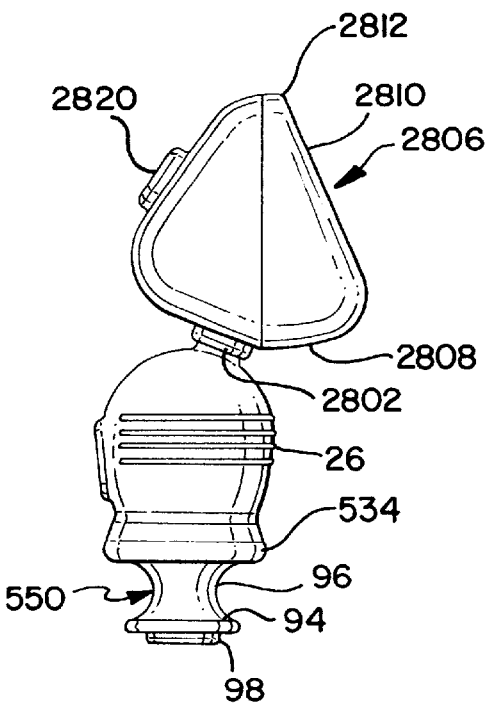
FIG. 51 is a side view of the nasal inhaler and mask shown in FIG. 50.
Figure 52:
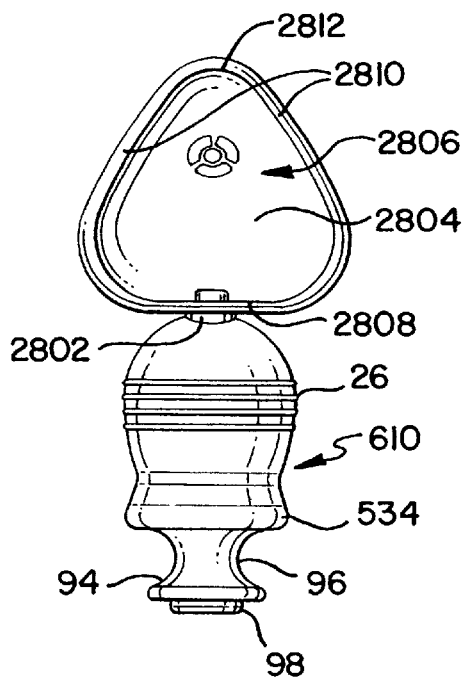
FIG. 52 is a front view of the nasal inhaler and mask shown in FIG. 50.
Figure 53:
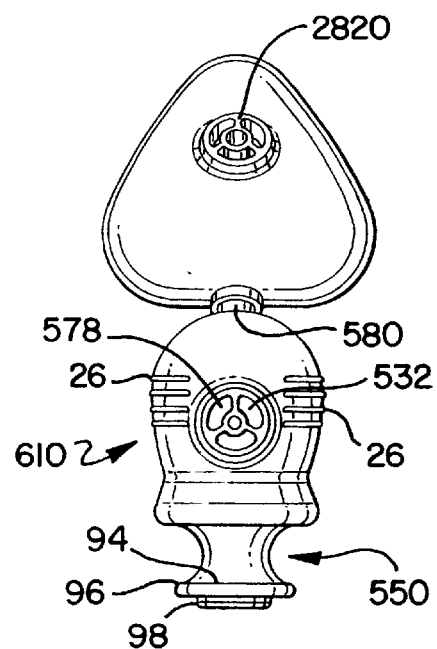
FIG. 53 is a rear view of the nasal inhaler and mask shown in FIG. 50.
Figure 54:
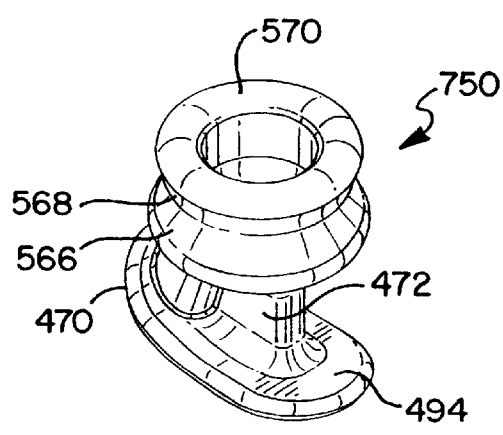
FIG. 54 is a perspective view of an alternative embodiment of an adapter.
Figure 55:
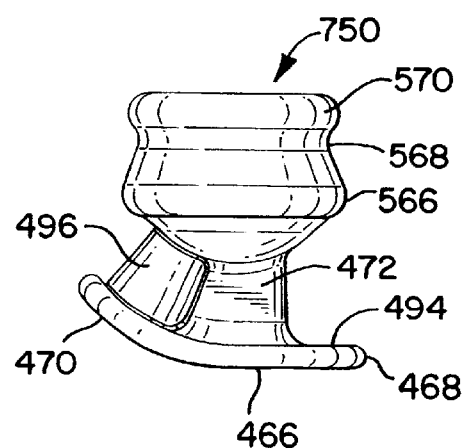
FIG. 55 is a side view of the adapter shown in FIG. 54.
Figure 56:
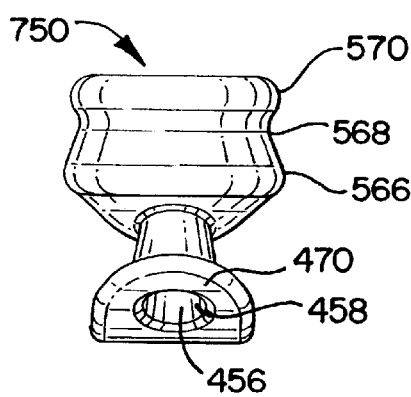
FIG. 56 is a front view of the adapter shown in FIG. 54.
Figure 57:
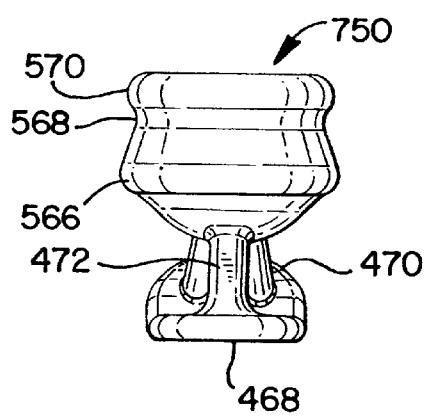
FIG. 57 is a rear view of the adapter shown in FIG. 54.
Figure 58:
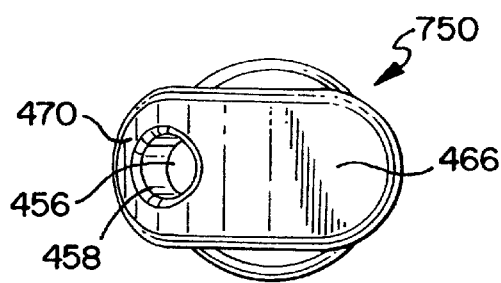
FIG. 58 is a bottom view of the adapter shown in FIG. 54.
Figure 59:
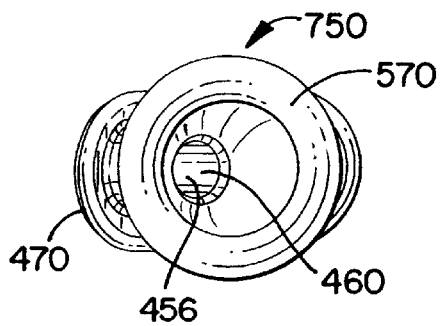
FIG. 59 is a top view of the adapter shown in FIG. 54.
Figure 60:
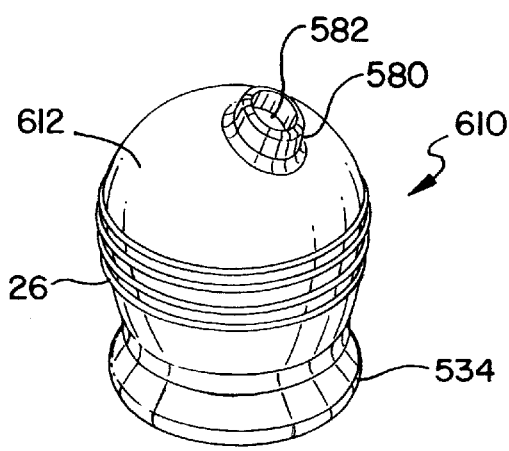
FIG. 60 is a perspective view of an alternative embodiment of a chamber.
Figure 61:
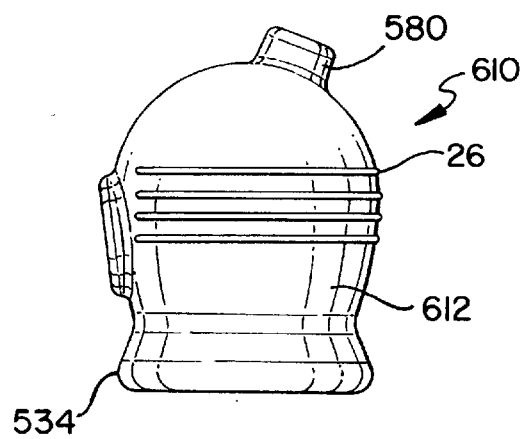
FIG. 61 is a side view of the chamber shown in FIG. 60.
Figure 62:
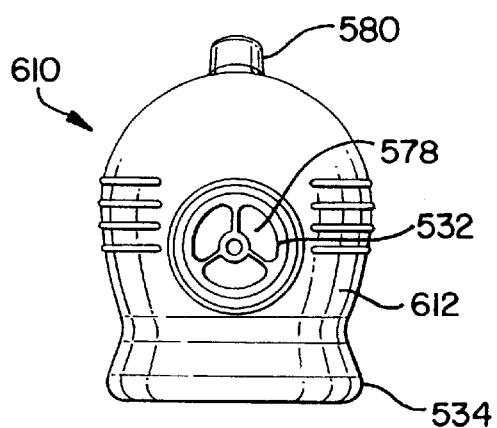
FIG. 62 is a front view of the adapter shown in FIG. 60.
Figure 63:
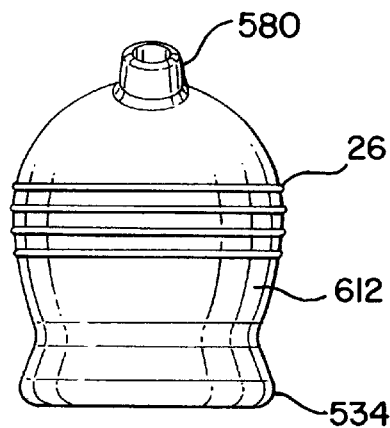
FIG. 63 is a rear view of the adapter shown in FIG. 60.
Figure 64:
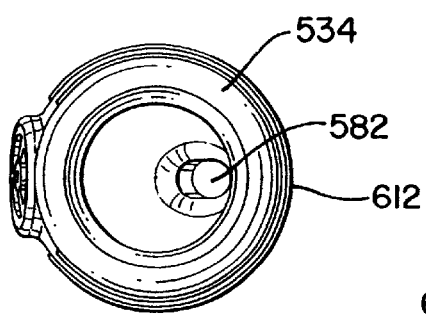
FIG. 64 is a bottom view of the adapter shown in FIG. 60.
Figure 65:
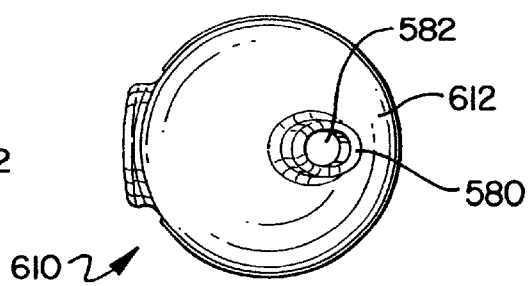
FIG. 65 is a top view of the adapter shown in FIG. 60.
Figure 66:
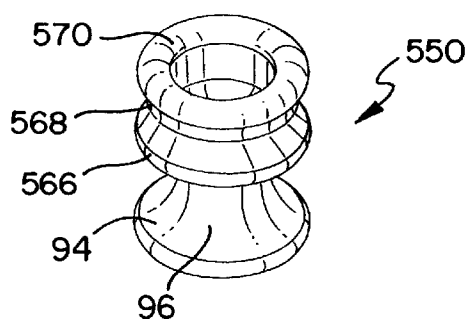
FIG. 66 is a perspective view of an alternative embodiment of an adapter.
Figure 67:
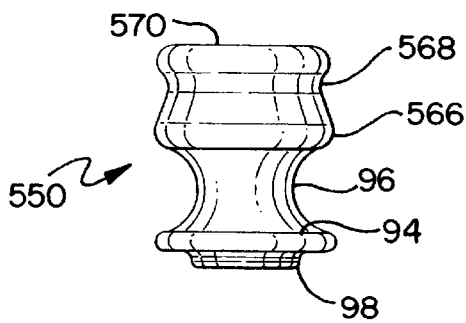
FIG. 67 is a side view of the adapter shown in FIG. 66.
Figure 68:
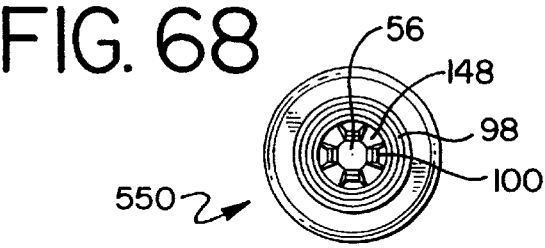
FIG. 68 is a bottom view of the adapter shown in FIG. 66.
Figure 69:
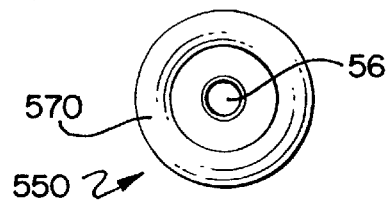
FIG. 69 is a top view of the adapter shown in FIG. 66.
Figure 70:
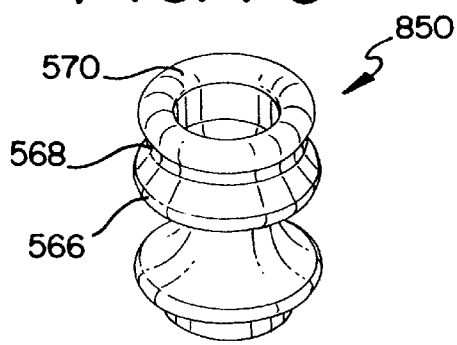
FIG. 70 is a perspective view of an alternative embodiment of an adapter.
Figure 71:
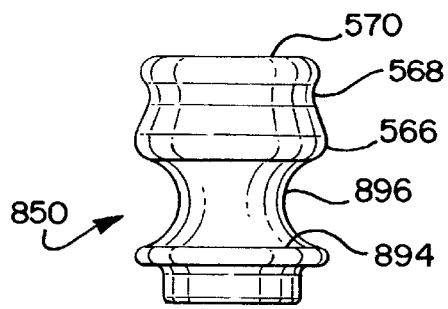
FIG. 71 is a side view of the adapter shown in FIG. 70.
Figure 72:
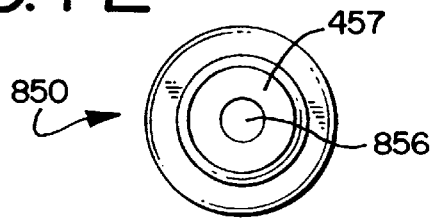
FIG. 72 is a bottom view of the adapter shown in FIG. 70.
Figure 73:
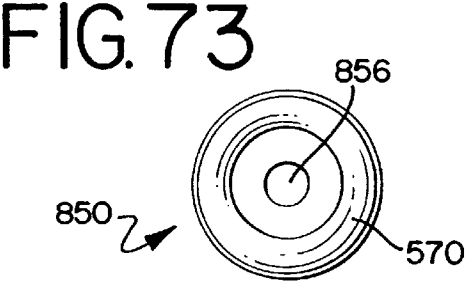
FIG. 73 is a top view of the adapter shown in FIG. 70.

As shown in FIGS. 1–4, an outlet 80 extends from the top of the holding portion 14 at a location spaced from and distal to the base portion 16 and the intake opening 28. In an exemplary embodiment, the outlet has a length of from about 6.35 mm to about 12.70 mm. The outlet 80 comprises an air exit passageway 82 that is in flow communication with the interior 24 of the chamber via an inlet port 86. The outlet preferably has an exterior contour, or shape, that is shaped to be received in the nasal vestibule cavity of the user, as illustrated in FIG. 38. An exit port 84 of the air exit passageway 82 preferably has an obround shape, although it should be understood that other shapes would also work, including for example an elliptical or circular opening. The size of the outlet can be altered and configured to accommodate the various sizes of the nasal openings, or vestibules, of the user, including for example outlets sized to accommodate a range of users from young children to adults. The outlet 80 is preferably oriented such that the air exit passageway 82, which is preferably linear, defines an axis 88 that is both non-parallel to and not coaxial with, the longitudinal axis 30 of the chamber, but rather form an angle ($\alpha$) therebetween. It should be understood that the air exit passageway could be parallel to and coaxial with the axis 30 and with the dosage inlet passageway.

Referring to FIGS. 1–8, the adapter 50 includes an insert portion 52 and a connector portion 54. The insert portion 52 is coupled with or connected to the base portion 16 of the chamber. The connector portion 54, which defines a dosage inlet passageway 56, can be configured to be connected with any number of various nasal delivery devices, including, for example, nasal spray containers (over-the-counter "OTC" or Prescription) and pressurized metered dose nasal inhalers.

In the exemplary embodiment of FIGS. 1–8, the adapter 50 includes a dosage inlet passageway 56 having an inlet port 58 and an exit port 60. Preferably, the adapter includes a funnel shaped cavity 64, which can have a conical or hemispherical shape. The cavity 64 opens into and defines and forms in part the interior volume 24 of the chamber. In the exemplary embodiment shown in FIGS. 1–8, the height of the chamber is approximately 76.71 mm and the width is approximately 55.88 mm, with the radial distance between the axis 30 and the portion of the wall having the valve openings 32 being approximately 23.23 mm. The interior volume of the nasal inhaler chamber, which includes the volume of the adapter cavity 64, is about 90 cm$^3$ (cc). It should be understood that other volumes would also work, including volumes in the range of between about 12 cc and about 144 cc, and preferably about 43 cc, particularly when the nasal inhaler is used with a pressurized metered dose container. Likewise, the dimensions of the chamber and adapter are provided as mere examples, and are not meant to limit in any way the scope of the invention. It should be understood that the output of the substance from the nasal inhaler is generally correlated to the volume of the chamber, with a smaller volume corresponding to a larger output absent any change to other geometrical parameters.

The insert portion 52 of the adapter 50 is preferably shaped to be inserted into the intake opening 28 of the base portion. As shown in the embodiment of FIGS. 1–8, the insert portion 52 preferably includes an upper circumferential wall 62, which defines in part the cavity 64. Circumferential ribs 51 are formed around the periphery of the wall 62 to frictionally and sealably engage the interior surface of the chamber base. A bottom of the insert portion 52 is flared out to form an annular stop member 66, which abuts the bottom edge or rim 34 of the base portion when the adapter is inserted into the base portion 16 of the chamber. A circumferential groove 68 or recess is formed around the periphery of the adapter 50 between the upper wall 62 and the stop member 66. The groove 68 is dimensioned and shaped to receive the enlarged bottom edge 34 of the base portion 16 in a snap-fit engagement, so as to thereby define a detent. In this way, the adapter 50 is releasably connected to the chamber 14 in a secure engagement suited for operation by the user.

The upper edge or rim 70 of the insert portion extends or protrudes slightly into the interior of the chamber, as best shown in FIG. 4, to form a circumferential solution trap between the rim 70 and the chamber wall 18. Any excess substance, or discharge from the user, that may remain in the chamber, or be condensed on the interior surface 20 of the chamber wall, will run into the solution trap 72, and will thereby be prevented from running out from the adapter through the dosage inlet passageway 56.

It should be understood that the adapter could be connected to the chamber in ways other than the afore-described snap fit, for example by way of a friction fit or adhesives. Moreover, it should be understood that other detents, including various resilient tab members or biasing members, would also work in place of the rib and groove interface. It should be understood that the term "detent" means a catch or like device for positioning and holding one part in relation to another so that one part can be released by force to the other.

Two pairs of axially spaced grooves 74, or recesses, are formed on opposite exterior sides of the adapter in alignment with the tab members 36 formed on the base portion of the chamber. As the insert portion 52 is inserted into the base portion 16, the tab members 36 are received in the recesses 74 and thereafter prevent the adapter 50 from being rotated about its longitudinal axis relative to the chamber, thus securing the proper alignment between the valve members and the valve openings.

The wall 62 defining the upper portion of the insert portion includes a pair of opposing U-shaped slots 76, or openings, which define a pair of flexible valve members 78, configured as flaps. Preferably, the portion of the wall forming the flaps is thinner than the remainder of the wall 62 as shown in FIG. 5. A rib 92 extends longitudinally between the valve members to increase the rigidity of the insert potion. The valve members 78 flex or pivot about the rib portion 92 to form an opening in the wall. The valve members 78 are positioned to be aligned with the valve openings 32 formed in the base portion when the adapter is connected with the chamber. As described above, the interface between the tab members 36 on the chamber and the recesses 74 formed in the adapter prevent the adapter from being rotated about the longitudinal axis 30 relative to the chamber, and thereby maintain the alignment of the valve members 78 and the valve openings 32.

Each of the valve member flaps has a surface area that is larger than the height of the valve opening 32, and the valve members therefore extend across the entirety of the valve opening 32 and are engaged with the interior surface 20 of the base portion when in their normal unflexed position. In this way, the flexible valve members 78, in combination with the valve opening 32, form a one-way valve, which allows air to enter the valve opening as it pushes back or flexes the valve members away from the valve opening, but which does not allow air to exit the valve opening by virtue of the engagement of the valve member 78 with the interior surface 20 of the chamber wall 18.

It should be understood that the connection of the chamber and adapter could be reversed, with the base of the chamber being inserted into an opening or cavity formed in the insert portion of the adapter. In such an embodiment, the adapter would preferably include a valve opening in the upper wall of the insert portion, while the chamber would be configured with a flexible valve member that overlies the interior surface of that wall in alignment with the valve opening.

The connector portion 54 further includes a circumferential rim 98 extending axially from the bottom thereof. The rim 98 defines the entry port 58 for the dosage inlet passageway 56, which preferably has a generally frusto-conical shape. Alternating raised and axially extending ribs 100 are arranged circumferentially around the interior surface of the dosage inlet passageway 56 and form alternating recesses 48 or grooves therebetween. The ribs 100 are preferably tapered from the bottom of the connector portion towards the top thereof, as shown in FIG. 4.

The connector portion 54 further includes a circumferential rim 98 extending axially from the bottom thereof. The rim 98 defines the entry port 58 for the dosage inlet passageway 56, which preferably has a generally frusto-conical shape. Alternating raised and axially extending ribs 100 are arranged circumferentially around the interior surface of the dosage inlet passageway 56 and form alternating recesses 78 or grooves therebetween. The ribs 100 are preferably tapered from the bottom of the connector portion towards the top thereof, as shown in FIG. 4.

Preferably, the chamber 12 and adapter 50 are made of a synthetic rubber material, and preferably of a silicone material, with the actuator preferably made of a more rigid type rubber than the chamber. In one embodiment, the chamber and actuator can be made transparent. Of course, it should be understood that the chamber and adapter could be made of a more rigid material, including, for example, plastic. It also should be understood that the chamber and adapter could be formed as a single integral unit. In such an embodiment, the chamber preferably comprises a lower adapter portion preferably configured as a handle, and a dosage inlet passageway formed therein.

Referring to FIG. 6, a nasal delivery device 40, or container, is shown as including a dispensing portion 42, preferably configured as a nozzle. The nozzle preferably has a frusto-conically shaped exterior terminating at a tip, which includes an opening 44. The dispensing portion is disposed, or inserted into the dosage inlet passageway 56 of the adapter. When connected, the nasal inhaler and container form a nasal inhaler assembly. Preferably, the dispensing portion engages the ribs 100 with a friction fit. The grooves or passageways 48 formed between the ribs 100 allow for a small amount of air to be drawn into the chamber between the exterior of the dispensing portion 42 and the interior surface defining the dosage inlet passageway 56.

Alternatively, and preferably, the grooves 48 formed between the ribs 100 end before reaching the narrowest portion of the passageway, such that the dispensing portion is sealingly engaged by the interior surface of the dosage inlet passageway 56. The grooves allow the dispensing portion to be more easily inserted into the dosage inlet passageway and/or prevent it from sticking to the interior surface, and also permit the adapter to accommodate dispensing portions having a range of diameters.

In the embodiment which allows air to be drawn through the grooves, the user preferably concurrently inhales with the compression of the chamber and/or actuation of the container. In yet another alternative embodiment, the interior surface of the dosage inlet passageway is smooth, or includes a circumferential rib, gasket or ring seal, that sealingly engages the dispensing portion or nozzle so as to not permit the entry of air therebetween.

The container 40 further comprises a holding portion 38 that holds a substance to be dispensed through the nasal inhaler. The container 40 further comprises a pump portion 46 or actuator that is reciprocally moveable relative to the holding portion. In operation, the user actuates the pump portion 46, or actuator, while gripping the handle 96. The user moves the pump portion 46, or actuator, towards the holding portion 38 and the connected adapter 50 so as to effect a discharge of the substance contained in the holding portion. The spray or other discharge is directed through the dispensing portion 42 and into the interior volume 24 of the chamber, and in particular, is directed at a top portion of the interior of the chamber, rather than at the air exit passageway, due to the afore-described configuration of the adapter and chamber.

Figure 34:
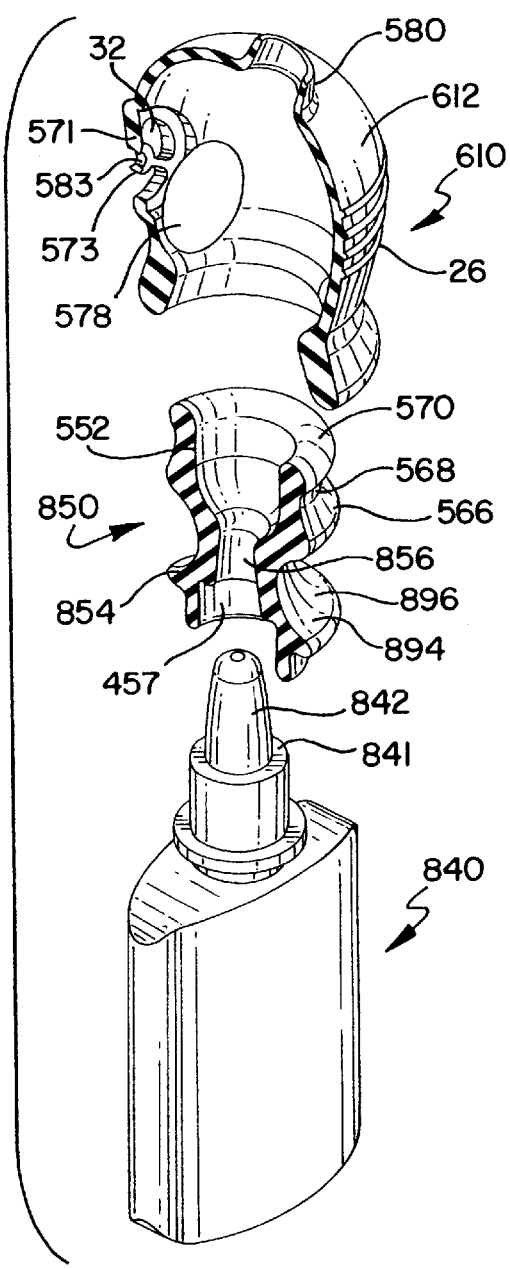
FIG. 34 is an exploded perspective view of the nasal inhaler and container shown in FIG. 33, with the nasal inhaler shown in cross-section.

It should be understood that the substance could take many forms, depending upon the type of nasal delivery device being used and/or upon the type of ailment being treated. For example, the nasal delivery device can take the form of a spray-pump container or bottle, as shown for example in FIGS. 6–8. Alternatively, it can take the form of a pressurized metered dose nasal inhaler, as shown in FIG. 22, or it can take the form of a simple squeeze-type bottle, as shown in FIG. 34. The substance can exit the container in the form of a dry powder or as a spray, in aerosol or aqueous form. The term "aerosol" means a suspension of fine solid or liquid particles in a gas, including air. Exemplary substances can include anti-cholinergic agents, adrenegically acting decongestants, topical buffering compounds and corticosteriod anti-inflammatory agents for treatments of various upper respiratory ailments, including sinusitis, allergic conditions, reactive airway diseases and rhinitus. The substance can also include various pain medications and insulin, which can be used to treat, for example, migraines and diabetes respectively. Of course, it should be understood that the nasal inhaler can be used with any substance which is capable of being introduced into a chamber and thereafter dispensed through an air exit passageway in response to the inhalation of a patient, the compression of the chamber, the actuation of the container, and/or some combination of those activities, and is not limited to the various substances herein described, or to the treatment of the various ailments herein described. The term "dosage" means the amount of substance dispensed in response to an actuation of the container. The amount of substance in each dosage can be metered, such that the amount remains relatively constant upon each actuation, or it can vary depending on the actuation force applied by the user. It should be understood that, just as the nasal inhaler can be used without the user affirmatively inhaling, the inhaler also can be used without an actuation of the container. For example, the user can entrain the substance, e.g., a dry powder, into the chamber by generating an air flow through inhalation or compression of the chamber.

In an alternative embodiment of the nasal inhaler 110, best shown in FIGS. 9–12 and 27, the holding portion 114 of the chamber has a spherical shape. An outlet platform 190 extends from a top and side of the chamber. A right and left nose plug 181, 180 extend from the platform on opposite sides thereof. An outlet 183 extends from a middle of the platform and is positioned between the pair of nose plugs. The nose plugs 180, 181 do not contain an air exit passageway, but do comprise an exterior contour that is shaped to be received in the nasal vestibule of the user, such that the user can plug one of their nostrils while inhaling through the other nostril. The nose outlet 183 is spaced from each of the right and left nose plugs 180, 181 so as to approximate the distance between the nostrils of the user. If treatment is recommended in the right nostril of the user, the left nose plug 181 can be inserted into the left nostril of the user while the outlet 183 is inserted into the right nostril. Conversely, if treatment is recommended for the left nostril, the right nose plug 180 can be inserted into the right nostril and the outlet 183 can be inserted into the right nostril. Of course, the nasal inhaler can be used to administer a substance to a user through both nostrils by successive insertion of the outlet 183 into the right and left nostrils respectively, or vice versa. The outlet includes an air exit passageway 182. It should also be understood that the nasal inhaler could be configured with a pair of outlets that can be inserted into the right and left nostrils at the same time. In yet another embodiment, the nasal inhaler comprises a single outlet and a single nose plug. In operation, the device can be rotated such that the outlet and nose plug can be inserted concurrently and interchangeably in the right and left nostrils.

Figure 11:
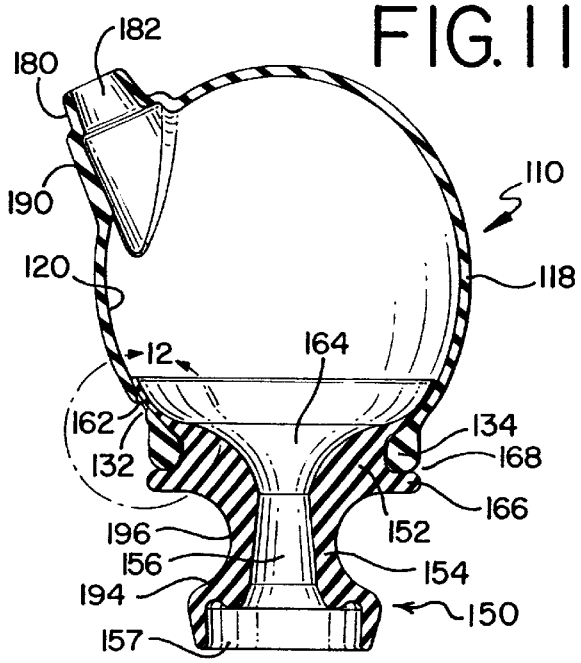
FIG. 11 is a cross-sectional side view of the nasal inhaler shown in FIG. 9.
Figure 12:
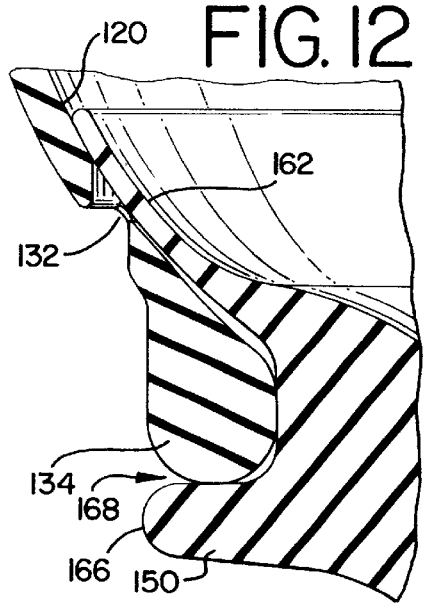
FIG. 12 is an enlarged partial view of a portion of the nasal inhaler shown in FIG. 11.
Figure 17:
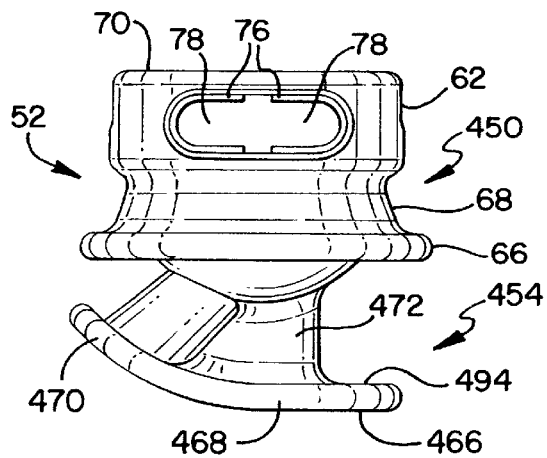
FIG. 17 is a side view of an alternative embodiment of an adapter.
Figure 18:
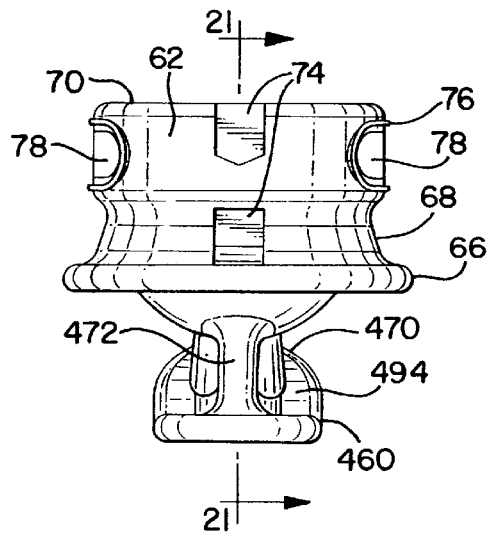
FIG. 18 is a front view of the adapter shown in FIG. 17.
Figure 19:
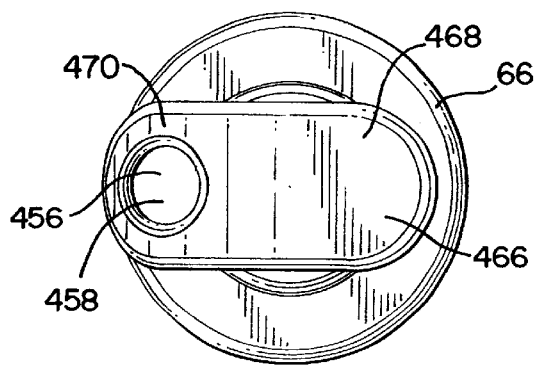
FIG. 19 is a bottom view of the adapter shown in FIG. 17.
Figure 20:
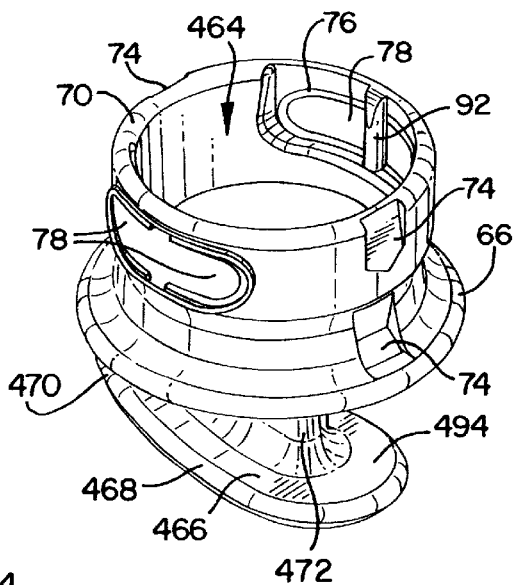
FIG. 20 is a top perspective view of the adapter shown in FIG. 17.
Figure 21:
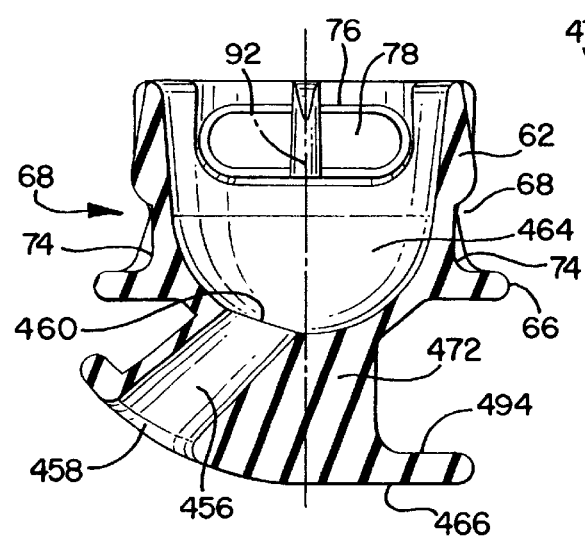
FIG. 21 is a cross-sectional side view taken along line 21—21 of FIG. 18.

As best shown in FIGS. 11 and 12, the adapter 150 comprises an insert portion 152 having a thin, flexible interior skirt 162 that extends upwardly along the interior surface 120 of the chamber wall and is sealingly engaged therewith. The skirt 162 overlies a plurality of valve openings 132 formed in the chamber wall 118. As shown in FIG. 12, air is drawn through the valve opening 132 during inhalation and causes the skirt 162 to flex away from the interior surface 120 of the wall 118. As such, the skirt 162 and valve opening 132 form a one-way valve, which prohibits air from exiting through the valve opening to the exterior of the chamber by virtue of the skirt engaging the chamber wall. The insert portion 152 further comprises a stop member 166 and a groove 168, which receives an enlarged lower edge 134 of the chamber. A cavity 164 is formed in the insert portion and opens into and defines in part the interior volume of the chamber.

Figure 27:
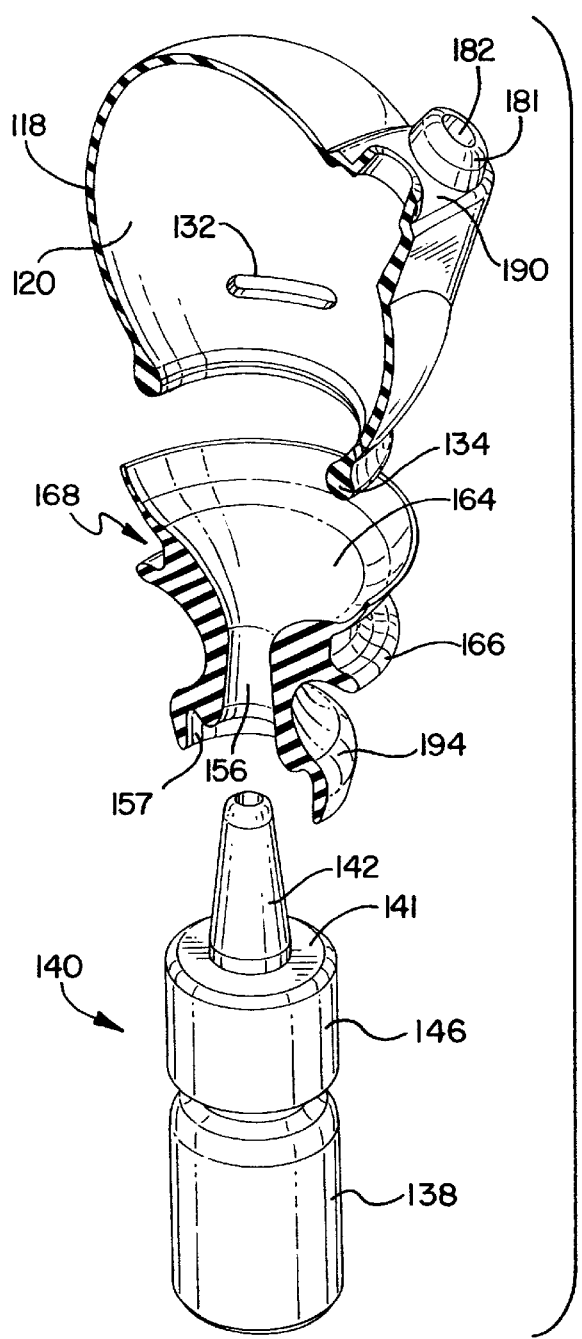
FIG. 27 is an exploded top perspective view of the nasal inhaler and container shown in FIG. 10, with the inhaler shown in cross-section.
Figure 28:
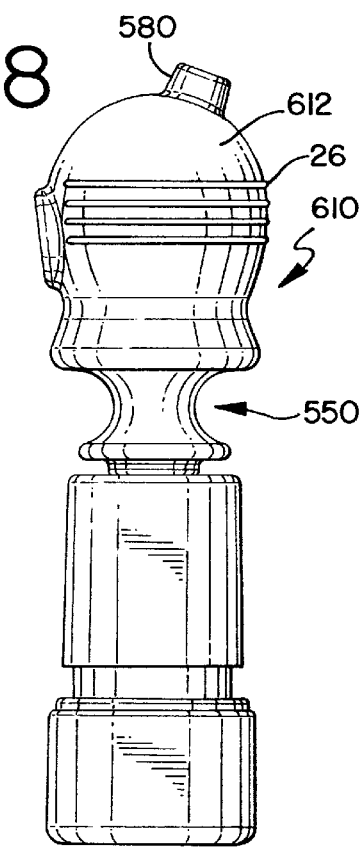
FIG. 28 is a side view of an alternative embodiment of a nasal inhaler and a container.
Figure 29:
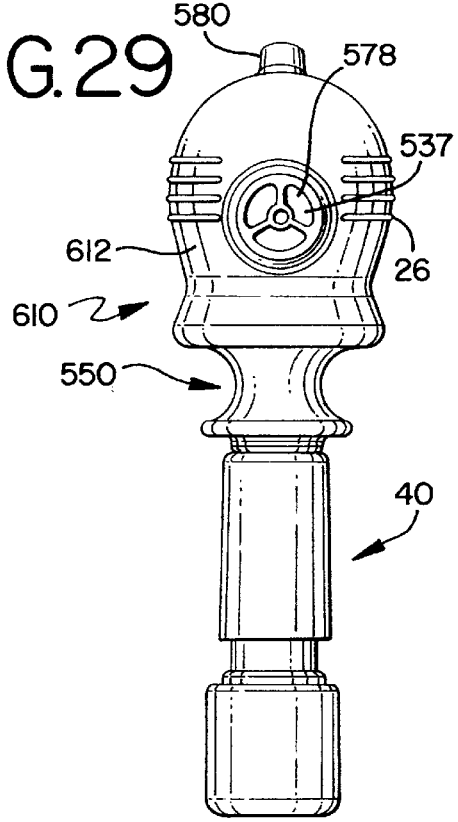
FIG. 29 is a rear view of the nasal inhaler and container shown in FIG. 28.
Figure 30:
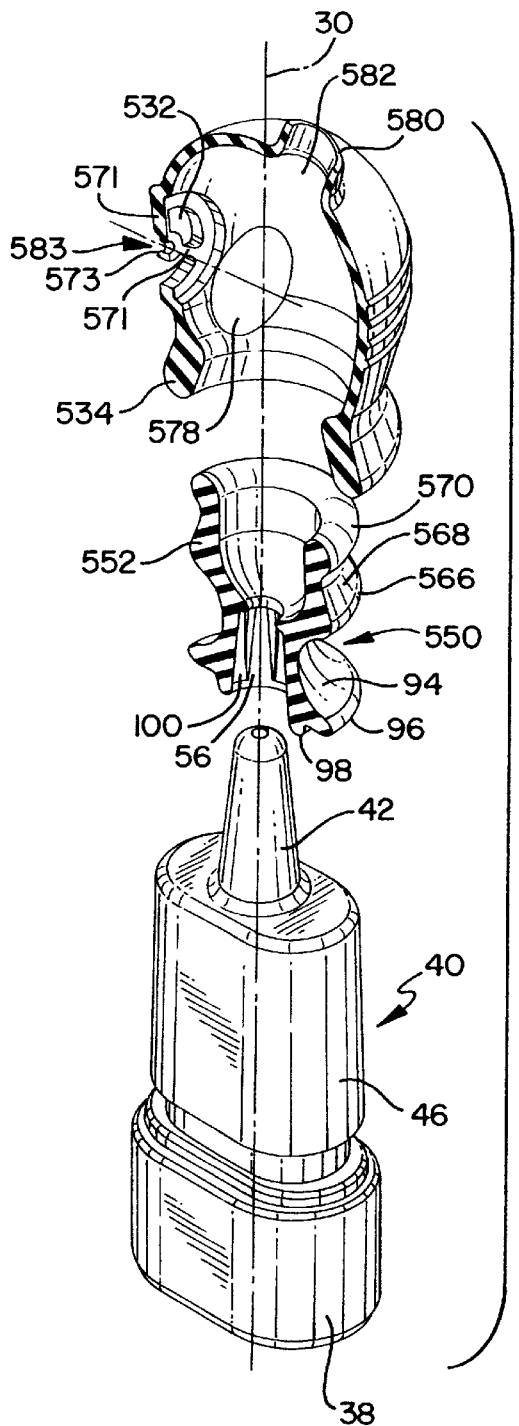
FIG. 30 is an exploded top perspective view of the nasal inhaler and container shown in FIG. 28, with the nasal inhaler shown in cross-section.
Figure 31:
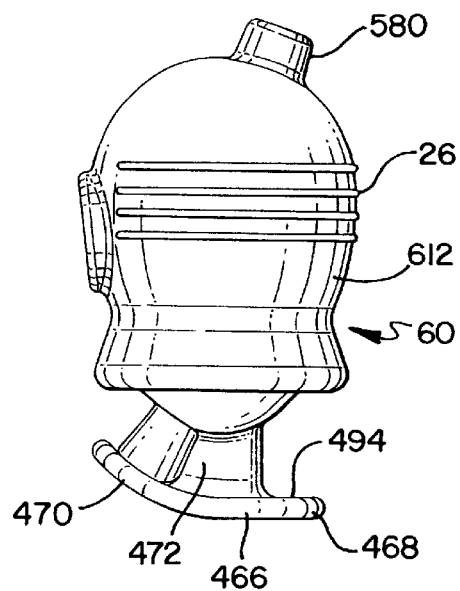
FIG. 31 is a side view of an alternative embodiment of a nasal inhaler.
Figure 32:
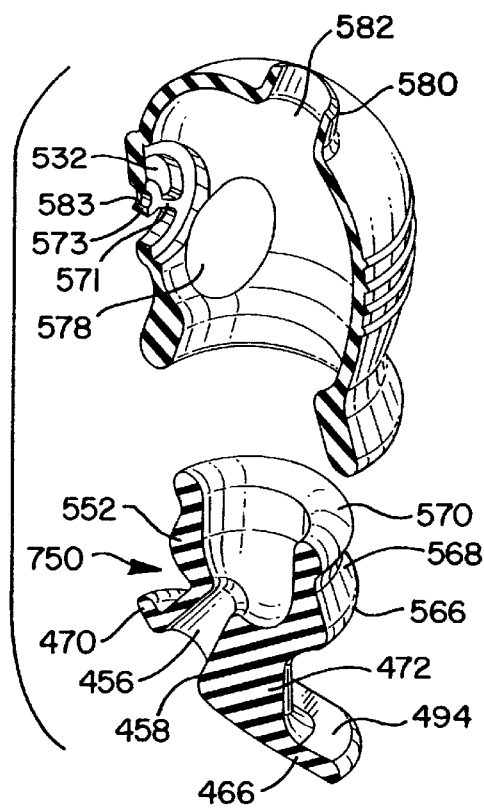
FIG. 32 is an exploded, cross-sectional perspective view of the nasal inhaler shown in FIG. 31.
Figure 33:
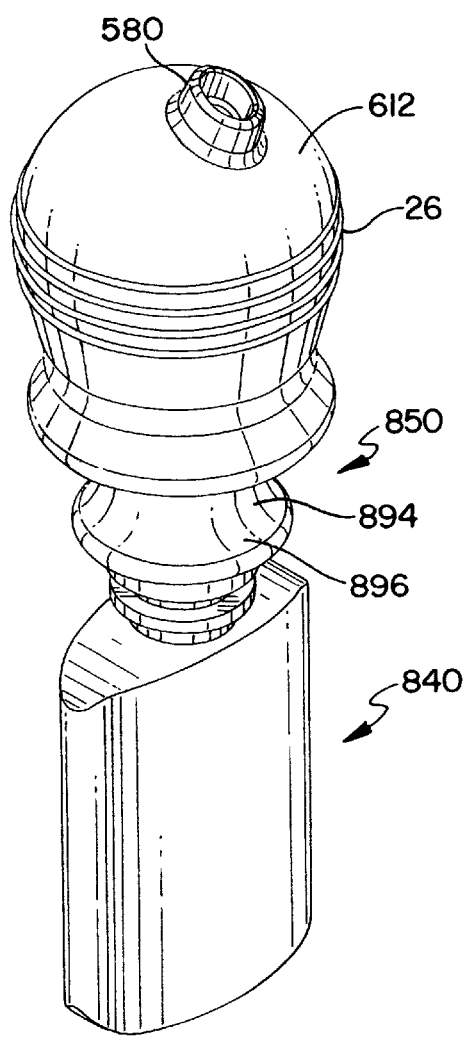
FIG. 33 is a top perspective view of an alternative embodiment of a nasal inhaler and of a container.

As shown in FIGS. 11 and 27, the connector portion 154 of the adapter has a outwardly opening cavity 157 shaped to receive a top shoulder portion 141 of a nasal spray device, or container 140, as a dispensing portion 142 is received in the dosage inlet passageway 156. The container 140 further includes a pump portion 138 and a holding portion 146. The connector portion further comprises a handle 196 having a grippable portion 194, configured as a shoulder.

Referring to FIGS. 15 and 16, the nasal inhaler 210 is shown as having a chamber 212 with an integrally formed adapter portion 250. In this embodiment, the adapter portion of the chamber 212 comprises a connector portion 254, which is configured as a handle 296 and defines the dosage inlet passageway 256 and a cavity 157 shaped to receive a shoulder portion 141 of the container 140. A single outlet 280 extends from a top portion of the chamber. The chamber 212 further includes a valve opening 232 formed in the side of the chamber wall. Preferably, the valve opening is circular. The chamber 212 further comprises a valve seat 266 defining the valve opening, which includes a raised or thickened portion having an annular groove 267 running circumferentially around the periphery of the opening, and a lip portion 268, which extends radially inward from the interior surface 220 of the chamber wall. The lip 268 forms a circular shoulder. A valve 278 includes an insert member 262 having an annular flange 264 with an outer portion that is received in the groove 267 to secure the valve 278 to the chamber. The insert member further comprises an annular rib 265 extending laterally from the flange and an interior annular flange 269 that defines an opening 271, with the rib 265 and interior flange 269 forming a recess.

A circular valve member 259 is dimensioned to be nested in the recess formed inside the annular rib 265 and is abutted against the interior flange 269. When the insert member is inserted into the groove 267 formed in the chamber wall, an outer circumferential edge of the valve member 259 is trapped between the interior flange 269 of the insert member and the lip portion 268. The valve member 259 further includes an elongated slot 253 that extends circumferentially around a portion of the valve member to define a valve portion 251 or flap that flexes or pivots about a hinge formed between the ends of the slot 253. The diameter of the valve portion 251 of the valve member is less than the diameter of the opening 268 defined by the lip portion, but is greater than the diameter of the opening 271 defined by the interior flange of the insert member. Accordingly, the valve portion can flex inwardly into the interior of the chamber during inhalation, but is biased toward and sealingly engages the flange 269 of the insert member at all other times.

Referring to FIGS. 13 and 14, an alternative embodiment of the nasal inhaler 310 is shown. The inhaler 310 comprises a larger, horizontally elongated chamber 312. In this embodiment, the adapter portion 350, which again is preferably formed integrally with the chamber, is oriented at an angle from the longitudinal axis 330 of the chamber. Moreover, neither a valve nor an air intake passageway is provided to be in flow communication with the interior of the chamber 312. Accordingly, to dispense the substance, the user preferably must squeeze or compress the chamber, with or without simultaneous inhalation. An outlet 383 and a nose plug 380 extend from an outlet platform 390, which preferably extends at substantially a right angle to the longitudinal axis 330 of the chamber. The adapter potion 350 comprises a connector portion 354 configured as a handle 396.

Referring to FIGS. 17–22, an alternative embodiment of an adapter 450 is shown. The adapter 450 is configured for use with a metered dose nasal inhaler. The adapter 450 can be used with any of the chambers described herein that do not have an integrally formed adapter portion. The adapter 450 includes an insert portion 52 that is the same as described above with respect to the nasal spray adapter. Accordingly, the features of the insert potion have been referenced with the same reference numbers and will not be herein described again. The connector portion 454 of the adapter includes a bottom wall 466 or foot portion having a flat portion 468 and a curved portion 470. A web 472 extends downwardly from the insert portion 52 and is connected to the bottom wall 466, which forms a handle 496. An inlet port 458 is formed in the curved portion 470 of the foot portion and opens into a dosage inlet passageway 456 that extends from the inlet port 458 through an enlarged portion of the web 472 at an angle. The dosage inlet passageway 456 terminates at an exit port 460 in flow communication with a cavity 464 formed in the insert portion 52. The dosage inlet passageway 456 oriented such that the substance exiting therefrom is aimed at the side of the adapter cavity 464 or at the side of the chamber, but is not coincident or coaxial with the air exit passageway 82, as shown for example in FIG. 22. The bottom wall 466 forming the foot portion preferably extends outwardly from the web 472 on all sides thereof to form a grippable surface 494 on top of the foot portion. The inlet port 458 and dosage inlet passageway 456 are shaped to receive a dispensing portion 442 of a pressurized metered dose nasal inhaler 440. In operation, the user can grasp the grippable surface 494 with their fore and middle fingers, as the web is disposed therebetween and with their finger tips preferably resting on the curved portion. At the same time, the user can use their thumb or other device to engage the bottom of a holding portion 446 of the container to effect an actuation thereof. Alternatively, the user can simply grasp the container and actuate it with the nasal inhaler connected thereto.

In an alternative embodiment of the nasal inhaler, best shown in FIG. 23, an outlet plug 331 includes a flexible lanyard 333 that is secured to the top of the chamber with a fastener, or by way of a detent or other type of snap fit. For example, the lanyard 333 can include an end 337 having an opening that is secured over a button member 335, which extends from the top of the chamber 12 as shown in FIG. 23. On the opposite end of the lanyard 333, the outlet plug includes a plug portion 339 that is shaped to be received in the exit port 84 of the air exit passageway 82. The plug portion 339 preferably engages the exit port in a friction fit when the inhaler is not in use so as to prevent foreign objects or materials, including dust and the like, to be introduced into the chamber.

Referring to FIGS. 24–26, an alternative embodiment of the nasal inhaler 510 is shown. The chamber 512 and adapter 550 assembly is collapsible, one within the other, so as to make the inhaler 510 more compact for storage and transportability. In particular, the adapter 550 is reciprocally and axially moveable along the longitudinal axis 530 between a retracted position and an extended position. As shown in FIG. 26, the adapter 550 does not include a stop member, which would extend radially outward beneath and engage the bottom edge 534 of the chamber. Rather, the insert portion 552 of the adapter includes an upper and lower rib portion 570, 566 that form a circumferential groove 568 or indentation therebetween. The groove 568 is shaped to mate with an upper and lower circumferential rib 535, 537 formed around the interior of the chamber when in the retracted and extended positions respectively. The chamber further includes an outlet 580 defining an air exit passageway 582. It should be understood that other types of detents and catch devices would also work to releasably secure the adapter to the chamber, including, for example, Velcro. When dispensing the substance, the lower rib 537 is disposed in the groove 568 to releasably engage the adapter in the extended position, as shown for example in FIG. 24. When the user is finished with the administration of the substance, the user pushes one or both of the container 40 and the adapter 550 so as to disengage the lower rib 537 from the groove 568. The user can thereafter move the adapter 550 and container 40 axially and upwardly into the interior volume of the chamber until the upper rib 535 is mated with the groove 568 so as to releasably secure engage the adapter 550 in the retracted position, as shown for example in FIG. 25. Preferably, an entirety of the adapter 550 is received in the interior volume of the chamber when in the retracted position. The movement of the adapter between the retracted and extended position can be successively performed as needed between treatments.

Referring to FIG. 26, the chamber 512 includes a valve opening 532 formed as three pie-shaped openings segmented by three spokes 571 meeting at a hub 573. A circular valve member 578 includes an axle portion 579 that is mated with an opening in the hub. A button 581 or catch is formed on the end of the axle and engages a seat 583 formed in the hub 573. Alternatively, a nut or like mechanical device can be engaged with the end of the axle after it is inserted through the hub opening. The axle 579 extends laterally from the valve member 578 at the approximate center of the valve member. The valve member 578 overlaps the valve openings 532 on the interior of the chamber. The valve member 578 is preferably flexible such that it can be moved away from the interior surface 520 of the chamber in response to air being drawn through the valve openings 532. The valve openings 532 and the valve member 578 form a center stem one-way valve.

It should be understood that the nasal inhaler 510 shown in FIG. 26 could alternatively be configured with a one-way valve formed by an opening in one of the chamber and the adapter that is covered with a valve member formed in the other of the chamber and the adapter, as explained above with reference to FIGS. 1–8, 9–12 and 27.

The terms "longitudinal" and "axial" as used herein are intended to indicate the direction of the axes defining the intake opening in the base of the chamber and the dosage inlet passageway, and also to indicate the direction of the reciprocal movement of the adapter relative to the chamber, as shown for example in FIGS. 24 and 25. The terms "top," "bottom," "side," "upwardly," "downwardly," "front" and "rear" are intended to indicate directions when viewing the inhalation devices as shown in the Figures, and when it is inserted into the nasal cavity of the user. It should be understood, however, that a user could use the nasal inhaler and container in any number of positions, including but not limited to the preferred upright position shown in FIG. 38.

Referring to FIGS. 28 and 60–65, a smaller embodiment of a nasal inhaler 610 is shown. The nasal inhaler 610 includes a center-stem one-way valve formed from a valve opening 532 and a flexible valve member 578. In an exemplary embodiment, the interior volume of the chamber 612, including the volume of cavity in the adapter, is preferably about 43 cc, while the chamber has a height of about 62.22 mm and a width of about 45.71 mm at the widest point. The adapter has a height of about 38.34 mm and a width of about 30.73 mm. Again, it should be understood that these dimensions are meant to be exemplary, and do not limit in any way the scope of the invention.

As shown in FIGS. 28–34, 54–59 and 66–73, either a first adapter 550, preferably used with a spray type container, and more preferably an aqueous spray container, a second adapter 750, preferably used with a pressurized metered dose nasal inhaler 440, or a third adapter 850, preferably used with a decongestant container 840, can be used interchangeably with the chamber 612. The second adapter 750 includes the same insert portion 552 as the first adapter 550 described above, and further includes a connector portion 454 similar to that described above with respect to FIGS. 17–22. In this way, it should be understood that an adapter can be configured with any combination of connector portions and insert portions herein described, such that the adapter can accommodate any combination of the various containers and chambers, respectively. It also should be understood that the nasal inhaler can be configured with any of the one-way valve embodiments described above, including a center-stem valve and a valve formed between the adapter and the chamber. It should be understood that other types of one-way valves, or check valves, not herein described would also work.

The third adapter 850 includes the same insert portion 552 as the first and second adapters 550, 750, and includes a connector portion adapted to mate with a spray container 840, similar to the connector portion described above with respect to FIG. 27. The spray container 840 is actuated by squeezing the container, which is made of a pliable material. The connector portion 854 has an outwardly facing recess 457 shaped and dimensioned to receive a shoulder portion 841 of the spray container 840, preferably with a friction fit. The dispensing portion 842, or nozzle, is inserted into the dosage inlet passageway 856. The connector portion 854 is configured as a handle 896 having a grippable shoulder portion 894.

Figure 35:
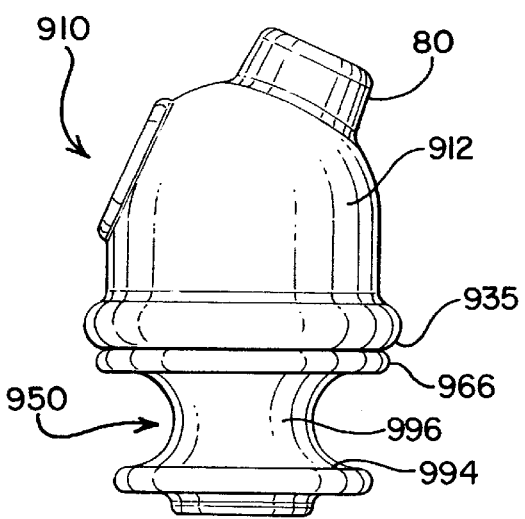
FIG. 35 is a side view of an alternative embodiment of a nasal inhaler.
Figure 36:
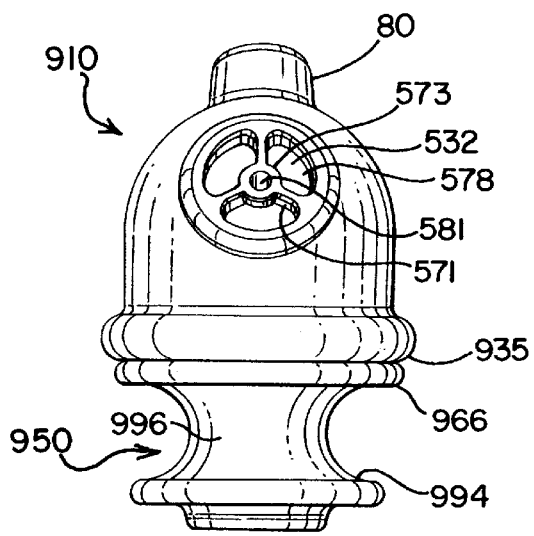
FIG. 36 is a rear view of the nasal inhaler shown in FIG. 35.
Figure 37:
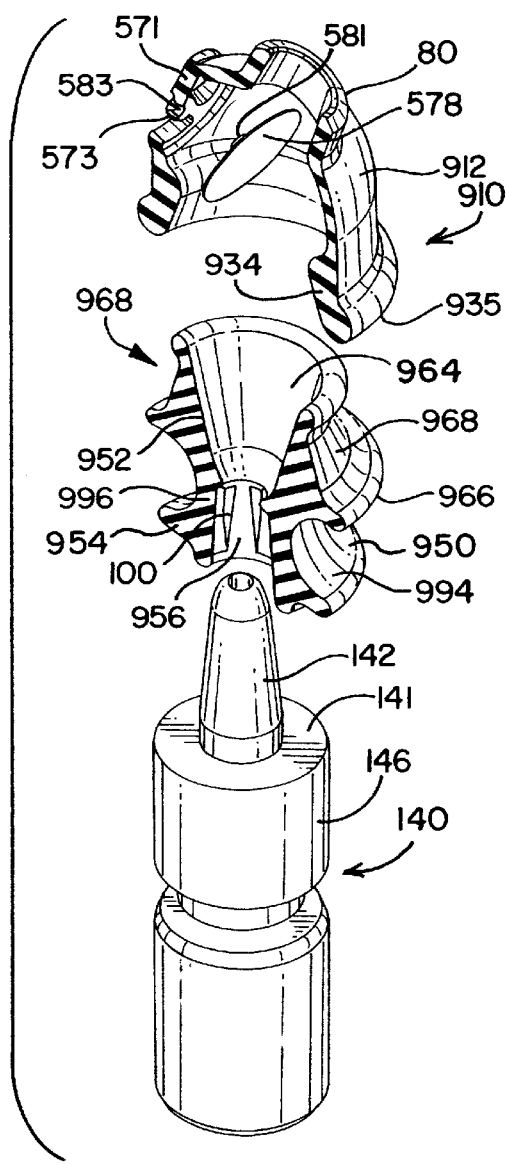
FIG. 37 is an exploded perspective view of the nasal inhaler shown in FIG. 35 and a container, with the nasal inhaler shown in cross-section.

Referring to FIGS. 35–37, yet another even smaller nasal inhaler 910 is shown. Preferably, the nasal inhaler 910 has in interior volume in the range of from about 12 cc to about 34 cc. In this embodiment, the insert portion 952, with its cavity, 964 makes up a larger proportion of the interior volume of the chamber. The adapter 950 preferably includes a circumferential groove 968 that mates with an radially enlarged interior rib portion 934 that extends circumferentially around the interior of the chamber 912. A stop member 966, forming a bottom of the groove, abuttingly engages the bottom edge of the chamber 935. The connector portion 954 of the adapter is again configured as a handle 996 having a grippable portion 994 and a dosage inlet passageway 956, which preferably includes longitudinally extending ribs 100 that engage the dispensing portion 142 of the container 140. A center-stem valve member 578 is mated with a valve opening 532 formed in the chamber 912 to form a one-way valve. An outlet 80 extends from the top of the chamber.

Figure 39:
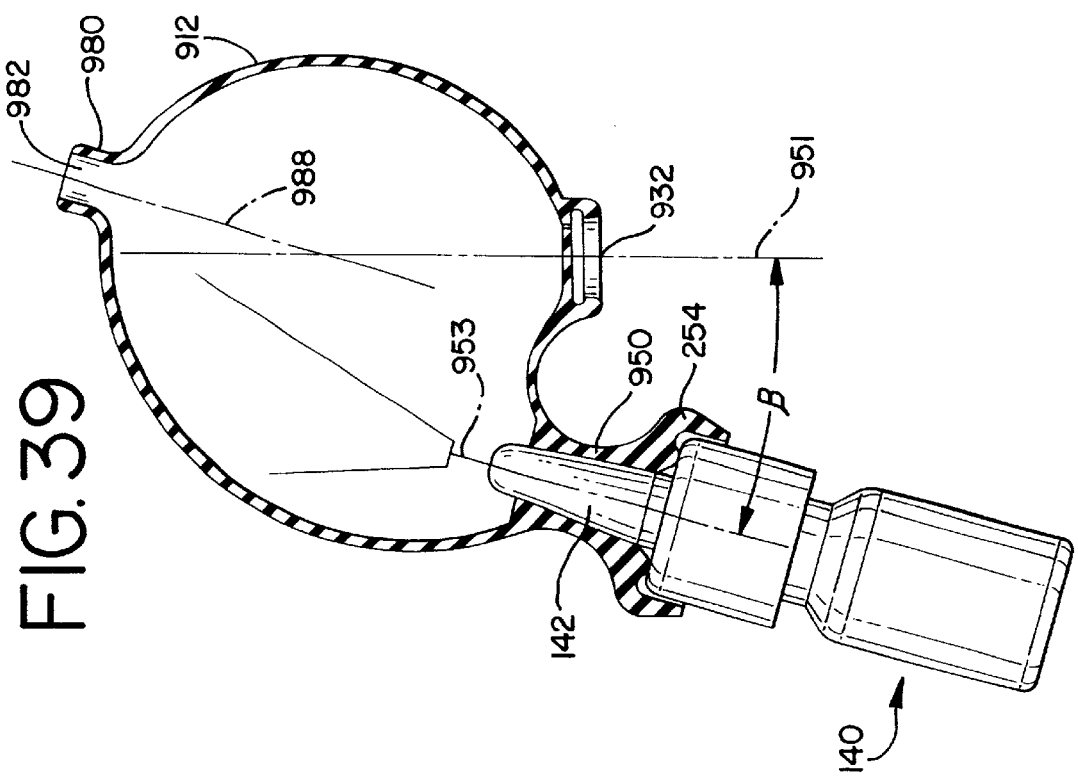
FIG. 39 is a partial cross-sectional side view of an alternative embodiment of a nasal inhaler with a container.

Referring to FIG. 39, the nasal inhaler 910 includes an integrally molded chamber 912 and adapter portion 950. The adapter portion comprises a connector portion 254 as described above with respect to FIGS. 15 and 16, with the same reference numbers being used to refer to corresponding features previously described. It should be understood that the adapter portion could be configured with any number of different connector portions as described above for connection with various container embodiments. The adapter portion, with its dosage inlet passageway, defines an axis 953 that is oriented at an angle (β) relative to a vertical axis 951 defined by a one-way valve 932, which opens to the exterior of the chamber. The one-way valve 932 is preferably positioned at the bottom of the interior of the chamber such that the flow entering the chamber will be directed toward the outlet and thereby aid in the evacuation of the chamber and also thereby resist and be directed against any substance that may fall back into the chamber. The one-way valve 932 preferably further includes a whistle, which sounds as air is drawn through the valve so as to provide the user with auditory notice that air is being expelled from the chamber. The whistle is preferably a reed whistle, which is preferably inserted between the valve and the atmospheric air. An outlet 980 having an air exit passageway 982 extends from a top of the chamber and defines an axis 988 that is non-coincident or non-coaxial with the axis 953.

Referring to FIGS. 40 and 41, another embodiment of a collapsible nasal inhaler 1010 is shown. The chamber 1012 includes a plurality of valve openings 1032 spaced circumferentially around the chamber adjacent the base 1016 thereof. A lower rim 1034 of the base is enlarged and shaped to releasably engage a circumferential groove 1068 formed on the adapter 1050. The adapter 1050 is similar to the adapter 150 as described above with respect to FIGS. 9–12, with the same reference numbers being used to refer to corresponding features previously described. The diameter of the rim 166 is decreased such that the adapter can be moved in and out of the chamber more easily. The adapter 1050 comprises a skirt 1062, which is slightly more shallow than the skirt 162, which cooperates with the valve openings 1032 to form a one-way valve. It should be understood that the adapter could be configured with any number of different connector portions as described above for connection with various container embodiments. The adapter 1050 further comprises a handle or strap 1063 that extends downwardly from the bottom rim 1098 of the connector portion. The strap includes an enlarged grippable portion 1065 formed at one end thereof.

When the nasal inhaler 1010 is not in use, the user can collapse the adapter 1050 and container to a retracted position within the chamber 1012, as shown in FIG. 41. In the retracted position, the strap 1063 extends through the intake opening 1028 and is disposed between the interior surface of the rim 1034 and the container 140. A portion of the strap, and in particular the grippable portion 1065, extends from the bottom of the chamber where it is exposed for grasping by the user. When the user desires to use the nasal inhaler 1010 with a container, the user grasps the strap 1063 and pulls the adapter 1050 and container 140 outwardly through the intake opening until the adapter 1050 is brought into a snap-fit engagement with the chamber 1012, preferably through the detent engagement of the rim 1034 and groove 1068, as shown in FIG. 40. In this position, the adapter 1050 and container 140 are in an extended position relative to the chamber 1012. The movement of the adapter relative to the chamber, with or without the container, between the retracted and extended position can be successively performed as needed.

Referring to FIGS. 42–47, another embodiment of a collapsible nasal inhaler 1110 is shown. The chamber 1112 is similar to the chamber 610 previously described, with like features identified with the same reference numbers, but further comprises a base portion 1116 that comprises a larger tapered portion 1117 along each side thereof. In this way, base portion 1116 can be provided with an intake opening that accommodates an oval, elliptical or oblong shaped container. Of course, the base portion can be made symmetrical with a circular intake opening to accommodate a cylindrical container. The base portion further comprises a rim portion 1134 extending laterally inward from the interior surface thereof. A one-way valve, shown as a center-stem valve, is formed in the side of the chamber 1112. In this embodiment, the pump portion or actuator of the container can be removed from the container. Instead, the adapter serves a dual function of adapter and actuator. As such, a single part replace two parts and thereby reduces the costs of manufacture and assembly.

An adapter 1150 is shown as including an elongated body 1151, which has an internal cavity shaped and dimensioned to receive a container, and preferably a holding portion 46, in a friction fit. An upper insert portion 1152 of the body 1151 includes an enlarged tab 1153 or detent extending laterally therefrom. In addition, an upper and lower rib 1155, 1157 are longitudinally spaced below the tab 1153 on the exterior of the body 1151. The tab and the upper rib 1153, 1155 are spaced so as to capture the rim portion 1134 of the chamber base therebetween in a snap-fit engagement when the adapter is in the extended position relative to the chamber. The tab and upper rib, in combination with the rim, form a detent.

The lower connector portion 1154 of the body comprises a pair of wings 1196, or handles, that extend laterally from each side of the body. Each wing has an upper concave surface 1197, which is shaped to mate with a user's finger. The lower ribs 1157 are spaced from the upper surface 1197 so as to capture the rim portion 1134 of the chamber base therebetween in a snap-fit engagement when the adapter is in the retracted position, as shown for example in FIGS. 45 and 46. In this way, the wings 1196 act as a stop member to prevent the adapter from being inserted all of the way into the interior of the chamber when in the retracted position. Moreover, the surface of the wings abuts the bottom of the chamber so as to prevent the user from grasping the wings and prematurely actuating the container. At the same time, the wings 1196 provide a grippable handle for use in actuating the container when the adapter is in the extended position. Movement of the adapter relative to the chamber, with or without the container, between the retracted and extended position can be successively performed as needed.

Referring to FIGS. 48–53, a mask 2800 is shown as having an inlet port 2802, which is connected to the outlet 580 of the nasal inhaler by inserting one in the other. It should be understood that the inlet port can be inserted into the outlet, or vice versa, the outlet can be inserted into the inlet port. The mask further comprises a cavity 2804 and a face-receiving opening 2806 defined by an edge of the mask. The contour of the edge is configured to conform to and engage the face of the user. In particular, a bottom edge 2808 of the mask is curvilinear and is shaped to abut the face of the user above an upper lip portion of the user. Side edges 2810 of the mask extend upwardly from the bottom edge 2808 and are shaped to conform generally to the cheeks of the user on opposite sides of the nose of the user. The side edges 2808 generally meet at an upper juncture 2812, which is curved and shaped to mate with the upper exterior of the user's nose. When placed over the user's nose, the mask 2800 generally provides a cavity 2804 that surrounds the nose of the user wherein the substance can be inhaled by the user into the nasal cavity. As shown in FIGS. 48 and 94, the mask 2800 is shaped such that the nostrils of the user are generally exposed and overlying the outlet 580. In this way, the substance is generally directed into the nasal vestibule as it leaves the outlet 580. The mask may be used, for example, by a user that may have various nasal deformities that prevent the outlet from being inserted into the nasal vestibule.

In the embodiment shown in FIGS. 49–52, the mask 2800 includes an air exhalation valve 2820, which is preferably one-way. The exhalation valve 2820 permits the user to exhale through their nose, with the air passing through the exhalation valve, rather than being introduced back into the chamber. In a preferred embodiment, shown in FIG. 48, the mask 2800 does not include an exhalation valve, as it is preferred that the user exhales through their mouth such that the substance is not lost by being blown out through the nasal vestibule, or back into the chamber.

It should be understood with reference to the various embodiments described above that the various one-way valves, including the various valve openings and valve members, can be interchanged in the various embodiments. Likewise, the various outlet and nose plug configurations shown in the different embodiments can be used on any of the various chambers. Similarly, the base portions of the various chambers can be configured to mate with any of the various adapter insert portions as desired.

In operation of any of the devices described above, the user couples an appropriate adapter 50, 150, 450, 550, 750, 850, 950, 1050, 1150 with a chamber 12, 112, 512, 612, 912, 1012, 1112 by inserting the insert portion into the base of the chamber. A nasal delivery device or container 40, 140, 440 is then operably connected to the adapter, or the adapter portion of the chamber if integrally formed therewith, by inserting the dispensing portion 41, 141, 441 into the dosage inlet passageway 56, 156, 256, 456, 956. The air exit passageway 82, 182, 282, 582 is unplugged, if necessary, and the outlet 80, 180, 280, 580 is thereafter inserted into the nasal vestibule of a user. If the chamber is configured with a nose plug 183, 383, the nose plug optionally can be inserted in the other nasal vestibule of the user. Alternatively, the mask is connected to the outlet and is disposed over the nose of the user, preferably with the outlet directed towards the nostril opening of the user.

The user then actuates the container 40, 140, 440 while, preferably at the same time, inhaling through the air exit passageway 82, 182, 282, 582. As explained above, however, it should be understood that the nasal inhaler can be used without inhalation, or conversely, without actuation of the container. The handle 96, 196, 296, 396, 496, 896, 996, 1196 on the adapter allows the patient to actuate the container with his/her thumb in the same manner as if no nasal inhaler were connected to the container. The substance is dispensed into the interior of the chamber 12, 112, 512, 612, 912 at a first velocity, and is encapsulated in the chamber in the form of an aerosol cloud. As the user inhales, or as the chamber is compressed or the container actuated, the aerosol exits the chamber through the air exit passageway 82, 182, 282, 582 at a second velocity, which is preferably less than the first velocity, and preferably in direction angled from the direction of entry into the chamber. Because of the preferred non-coaxial (and the more preferred non-parallel) orientation between the dosage inlet passageway and the air exit passageway, the exit velocity can be reduced, and premature evacuation of the chamber is avoided. As the aerosol exits the outlet, the shape and orientation of the outlet 80, 180, 280, 580 directs the aerosol away from the septum and toward the desired target area, generally including the nasal turbinates. In these ways, the nasal inhaler can reduce, or avoid altogether, the painful discharge of the substance as it impacts the nasal membranes, for example, when administered directly by a pressurized metered dose inhaler. At the same time, the outlet, which is generally shorter than the typical nozzle, in combination with the reduced velocity, can help to avoid a deposit of the substance at the back of the nasal cavity, where it simply drains into the throat of the user, or conversely drains out the front of the user's nose.

Figure 74:
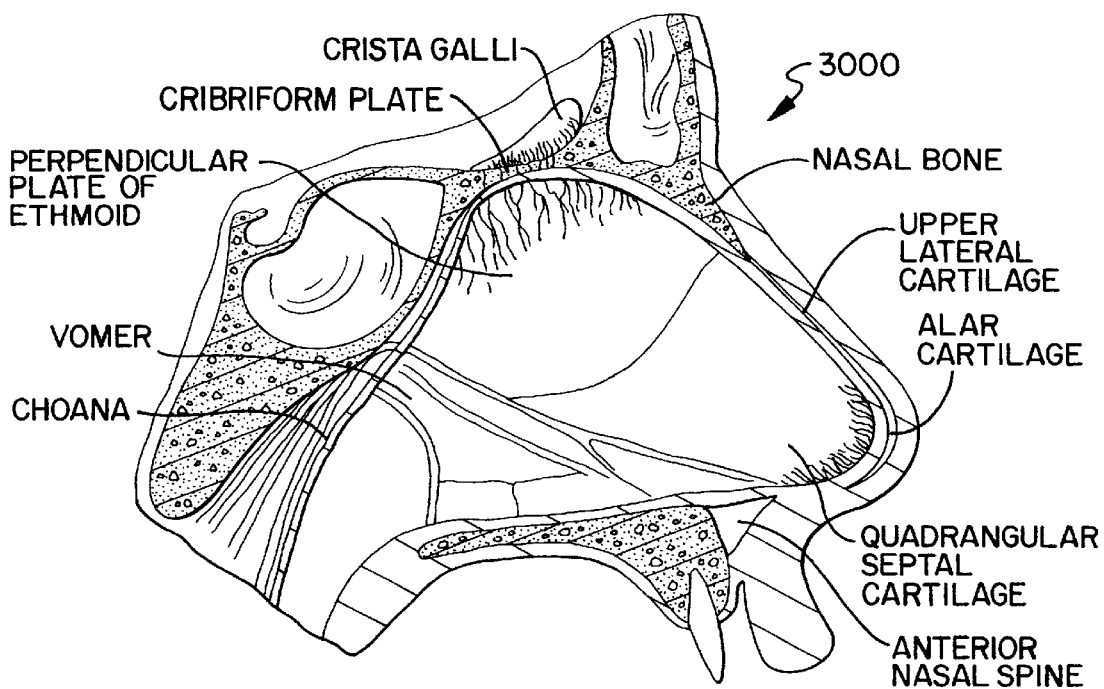
FIG. 74 is a view of the septum of the nose.
Figure 75:
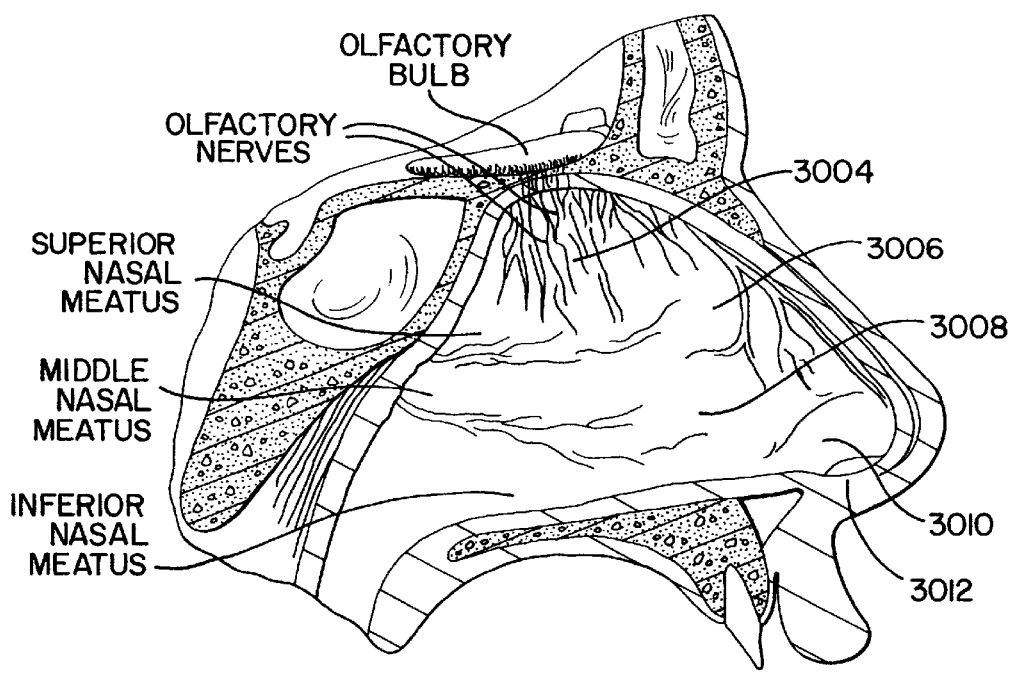
FIG. 75 is a view of the lateral wall of the nose.
Figure 76:
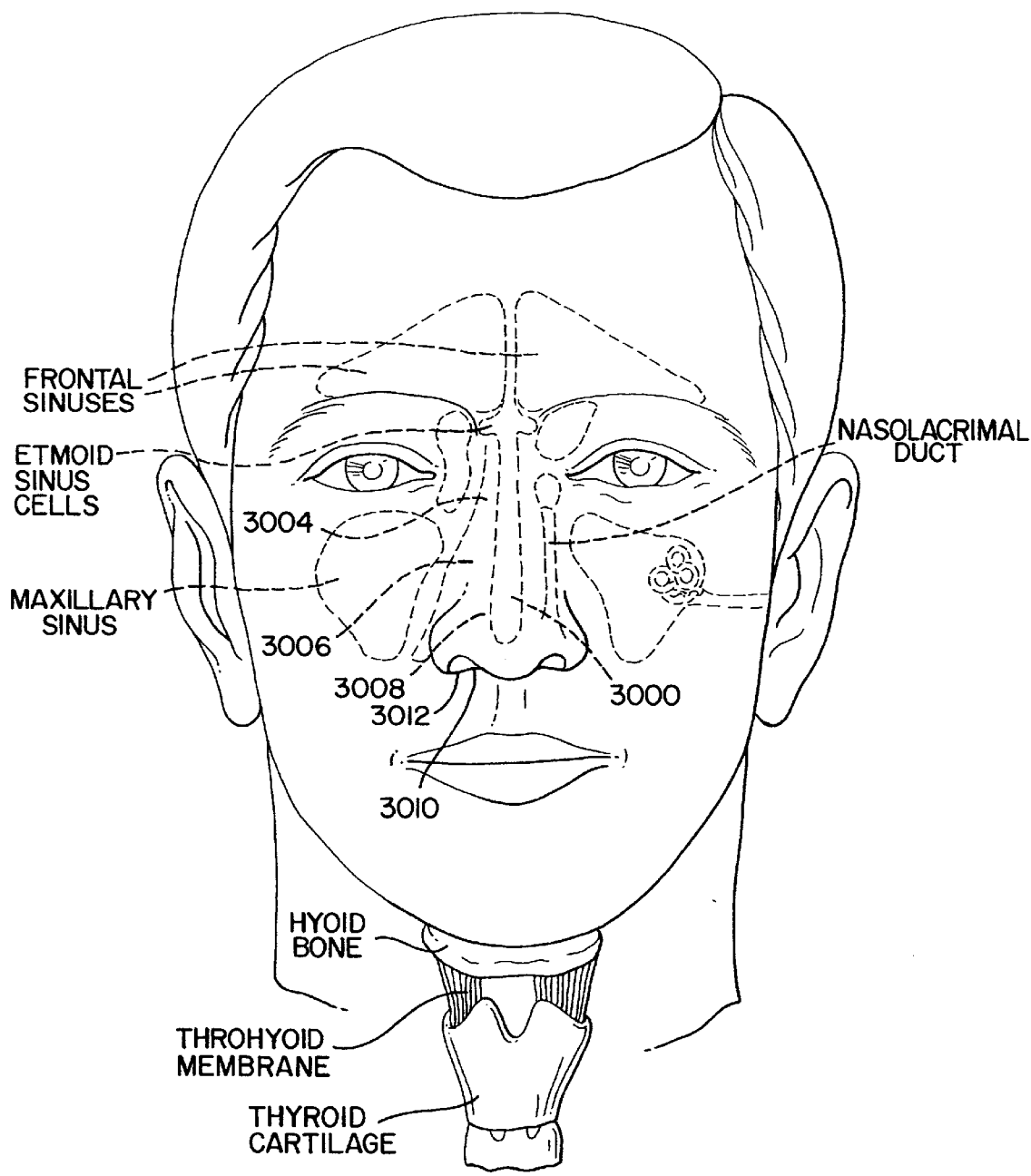
FIG. 76 is a front view of a user, with the nasal cavity area shown in partial cross-section.

Referring to FIGS. 74–76, the septum 3000 is a cartilage and bone structure that divides the nose into two halves, or two nasal cavities. It should be understood that the term "nasal cavity" includes the entire nasal passageway from the nostril to the throat of the user. The septum 3000 is covered with a thin membrane having a limited blood supply and is easily irritated by contact with various substances, in particular those that contain propellants, which is typically used with metered dose formulations. As best shown in FIGS. 75 and 76, the nasal turbinates, which can include the superior, middle and inferior turbinates 3004, 3006 and 3008, are formed along the lateral sidewall of the interior of the nasal cavity. The nasal vestibule 3010 is formed at the entrance to the nasal cavity at the nostril opening 3012.

During inhalation by the user, ambient air preferably enters the chamber 12, 112, 512, 612, 912 through the one-way valve and further entrains the substance, thereby allowing the user to evacuate fully the chamber. At the same time, the user can compress or squeeze the chamber, which is preferably flexible, to force the aerosol through the outlet. Patients with blocked nasal passages from nasal polyps, excess mucus, or nasal obstruction may not be able to inhale the aerosol and, therefore, a flexible chamber allows these patients to force the substance into the nasal passage with little or no inhalation. Because the valve is preferably one-way, compression of the chamber does not force or allow air to escape through the valve. Likewise, the one-way valve creates a positive pressure that prevents the user from exhaling into the chamber, which could compromise the substance entrained therein. Of course, it should be understood that the nasal inhaler would also work without a valve, one-way or otherwise. For example, the inhaler may simply include an air intake passageway that allows air to enter the chamber and aid in the evacuation thereof.

After the substance is administered, the user can plug the outlet so as to prevent the chamber from being contaminated. In addition, if using a collapsible embodiment of the nasal inhaler 510, the user can move the adapter 550 relative to the chamber 512, with or without the container connected thereto, from the extended position to the retracted position.

If the user is required to use different types of substances, and/or containers filled with such substances, the containers can be easily disconnected or removed from the connector portion of the adapter. Likewise, if the connector portion is not suited for coupling with a new container, the adapter can also be easily disconnected from the chamber. A new adapter suited for use with the new container can then be connected to the chamber by inserting the insert portion into the base of the chamber until those members are releasably engaged. The container can then be inserted into the connector portion, wherein the overall assembly is ready for use by the user. Conversely, if the user desires to use different chambers with a single container, different adapters having a connector portion suitable for connection with the container can be used to provide a suitable insert portion for mating with the desired chamber.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A nasal inhaler for introducing a substance to a nasal cavity of a user, said nasal inhaler comprising:
    a chamber having an interior and an exterior, wherein said chamber is made of a flexible material;
    an outlet comprising an exit passageway in flow communication with said interior of said chamber, said outlet shaped to be received in a nasal vestibule of the user;
    a one-way air inlet valve in one-way flow communication with said interior of said chamber at a first location spaced from said exit passageway, said one-way air inlet valve operative to permit said one-way flow of air from said exterior of said chamber into said interior of said chamber; and
    a dosage inlet passageway in flow communication with said interior of said chamber at a second location spaced from said exit passageway and from said first location.

2. The invention of claim 1 wherein said dosage inlet passageway is shaped to operably engage a container holding the substance.

3. The invention of claim 1 further comprising a plurality of outlets.

4. The invention of claim 1 further comprising a nose plug extending from said exterior of chamber adjacent said outlet, said nose plug shaped to be received in the nasal cavity of the user.

5. The invention of claim 1 further comprising a container, wherein said container comprises a dispensing portion disposed in said dosage inlet passageway.

6. A nasal inhaler for introducing a substance to a nasal cavity of a user, said nasal inhaler comprising:
    a chamber having an interior and an exterior;
    an outlet comprising an exit passageway in flow communication with said interior of said chamber, said outlet shaped to be received in a nasal vestibule of the user;
    a one-way air inlet valve in one-way flow communication with said interior of said chamber at a first location spaced from said exit passageway, said one-way air inlet valve operative to permit said one-way flow of air from said exterior of said chamber into said interior of said chamber;
    a dosage inlet passageway in flow communication with said interior of said chamber at a second location spaced from said exit passageway and from said first location; and
    an adapter defining said dosage inlet passageway, wherein said chamber comprises a base having an opening and wherein said adapter has an insert portion disposed in said opening of said base in a releasable engagement therewith.

7. The invention of claim 6 wherein said adapter comprises a handle having a grippable portion.

8. The invention of claim 6 wherein said chamber and said adapter are connected with a snap-fit engagement.

9. The invention of claim 6 wherein one of said chamber and said adapter comprise a rib and the other of said chamber and said adapter comprise a groove, wherein said rib is received in said groove.

10. The invention of claim 6 wherein one of said chamber and said adapter has a valve opening, and wherein the other of said chamber and said adapter comprises a flexible valve member overlying at least a portion of said valve opening on one of said interior of said chamber and an interior of said adapter, wherein said one-way valve is formed by said valve member overlying said valve opening.

11. The invention of claim 10 wherein said valve member comprises a pair of flexible portions overlapping portions of said valve opening.

12. The invention of claim 6, wherein said interior of said chamber is sized to receive said adapter, wherein said adapter is moveable between a retracted position wherein at least a portion of said adapter is positioned inside said interior of said chamber and an extended position wherein at least a portion of said adapter extends from said chamber.

13. The invention of claim 12 wherein said adapter is releasably engaged with said chamber in said retracted and said extended positions so as to prevent movement therebetween.

14. The invention of claim 13 wherein said adapter engages said chamber with a snap-fit when in said retracted and said extended positions.

15. A nasal inhaler for introducing a substance to a nasal cavity of a user, said nasal inhaler comprising:
- a chamber having an interior and an exterior;
- an outlet comprising an exit passageway in flow communication with said interior of said chamber, said outlet shaped to be received in a nasal vestibule of the user;
- a one-way air inlet valve in one-way flow communication with said interior of said chamber at a first location spaced from said exit passageway, said one-way air inlet valve operative to permit said one-way flow of air from said exterior of said chamber into said interior of said chamber; and
- a dosage inlet passageway in flow communication with said interior of said chamber at a second location spaced from said exit passageway and from said first location, wherein said air exit passageway defines a first axis and wherein said dosage inlet passageway defines a second axis, and wherein said first and second axes are offset.

16. A nasal inhaler for introducing a substance to a nasal cavity of a user, said nasal inhaler comprising:
- a chamber having an interior and an exterior;
- a plurality of outlets, each of said plurality of outlets comprising an exit passageway in flow communication with said interior of said chamber, and each of said plurality of outlets shaped to be received in a nasal vestibule of the user;
- a one-way air inlet valve in one-way flow communication with said interior of said chamber at a first location spaced from said exit passageways, said one-way air inlet valve operative to permit said one-way flow of air from said exterior of said chamber into said interior of said chamber; and
- a dosage inlet passageway in flow communication with said interior of said chamber at a second location spaced from said exit passageways and from said first location.

17. A nasal inhaler for introducing a substance to a nasal cavity of a user, said nasal inhaler comprising:
- a chamber having an interior and an exterior;
- an outlet comprising an exit passageway in flow communication with said interior of said chamber, said outlet shaped to be received in a nasal vestibule of the user;
- a pair of nose plugs positioned on opposite sides of said outlet and extending from said exterior of chamber adjacent said outlet, each of said nose plugs shaped to be received in the nasal cavity of the user;
- a one-way air inlet valve in one-way flow communication with said interior of said chamber at a first location spaced from said exit passageway, said one-way air inlet valve operative to permit said one-way flow of air from said exterior of said chamber into said interior of said chamber; and
- a dosage inlet passageway in flow communication with said interior of said chamber at a second location spaced from said exit passageway and from said first location.

18. A method for dispensing a substance into a nasal cavity of a user comprising:
providing a nasal inhaler comprising:
- a chamber having an interior and an exterior, wherein said chamber is made of a flexible material;
- an outlet comprising an exit passageway in flow communication with said interior of said chamber, said outlet shaped to be received in a nasal vestibule of the user;
- a one-way air inlet valve in one-way flow communication with said interior of said chamber at a first location spaced from said exit passageway; and
- a dosage inlet passageway in flow communication with said interior of said chamber at a second location spaced from said exit passageway and from said first location;
providing a container holding said substance, said container comprising a dispensing portion disposed in said dosage inlet passageway;
inserting said outlet into said nasal vestibule; dispensing said substance from said container into said chamber;
dispensing said substance from said chamber through said outlet; and
compressing said chamber during said dispensing of said substance from said chamber and thereby forcing said substance within said chamber through said outlet.

19. The method of claim 18 wherein said dispensing said substance from said chamber further comprises inhaling through said outlet and thereby drawing said substance through said outlet, wherein said inhaling further comprises drawing air into said chamber from said exterior of said chamber through said one-way valve.

20. A method for dispensing a substance into a nasal cavity of a user comprising:
providing a nasal inhaler comprising:
- a chamber having an interior and an exterior;
- an outlet comprising an exit passageway in flow communication with said interior of said chamber, said outlet shaped to be received in a nasal vestibule of the user;
- a one-way air inlet valve in one-way flow communication with said interior of said chamber at a first location spaced from said exit passageway; and
- a dosage inlet passageway in flow communication with said interior of said chamber at a second location spaced from said exit passageway and from said first location;
providing a container holding said substance, said container comprising a dispensing portion disposed in said dosage inlet passageway;
providing an adapter defining said dosage inlet passageway, wherein said adapter is releasably connected to said chamber;
inserting said outlet into said nasal vestibule;
dispensing said substance from said container into said chamber; and
dispensing said substance from said chamber through said outlet.

21. The invention of claim 20 wherein said adapter comprises a handle having a grippable portion, and wherein said dispensing said substance from said container further comprises gripping said grippable portion and said container.

22. The invention of claim 20 wherein said chamber and said adapter are connected with a snap-fit engagement.

23. The invention of claim 20 wherein one of said chamber and said adapter has a valve opening, and wherein the other of said chamber and said adapter comprises a flexible valve member overlying at least a portion of said valve opening on one of said interior of said chamber and an interior of said adapter, wherein said valve opening and said valve member form said one-way valve, and further comprising drawing air into said interior of chamber from said exterior of said chamber through said one-way valve and thereby forcing said flexible valve member away from said opening and into one of said interior of said chamber and said interior of said adapter.

24. The invention of claim 20 wherein said interior of said chamber is sized to receive said adapter, and further comprising moving said adapter between a retracted position wherein at least a portion of said adapter is positioned inside said interior of said chamber and an extended position wherein at least a portion of said adapter extends from said chamber, and wherein said dispensing said substance comprises actuating said container when said adapter is in the extended position.

25. The invention of claim 24 further comprising releasably engaging said adapter with said chamber when said adapter is in said retracted and said extended positions so as to prevent movement between said adapter and said chamber.

26. A method for dispensing a substance into a nasal cavity of a user comprising:
providing a nasal inhaler comprising:
a chamber having an interior and an exterior; an outlet comprising an exit passageway in flow communication with said interior of said chamber, said outlet shaped to be received in a nasal vestibule of the user;
a one-way air inlet valve in one-way flow communication with said interior of said chamber at a first location spaced from said exit passageway; and
a dosage inlet passageway in flow communication with said interior of said chamber at a second location spaced from said exit passageway and from said first location;
providing a container holding said substance, said container comprising a dispensing portion disposed in said dosage inlet passageway;
inserting said outlet into said nasal vestibule;
dispensing said substance from said container into said chamber at a first velocity; and
dispensing said substance from said chamber through said outlet at a second velocity, wherein said second velocity is less than said first velocity.

27. A method for dispensing a substance into a nasal cavity of a user comprising:
providing a nasal inhaler comprising:
a chamber having an interior and an exterior;
an outlet comprising an exit passageway in flow communication with said interior of said chamber, said outlet shaped to be received in a nasal vestibule of the user;
a one-way air inlet valve in one-way flow communication with said interior of said chamber at a first location spaced from said exit passageway; and
a dosage inlet passageway in flow communication with said interior of said chamber at a second location spaced from said exit passageway and from said first location, wherein said air exit passageway defines a first axis and wherein said dosage inlet passageway defines a second axis, and wherein said first and second axes are not co-axial;
providing a container holding said substance, said container comprising a dispensing portion disposed in said dosage inlet passageway;
inserting said outlet into said nasal vestibule;
dispensing said substance from said container into said chamber; and
dispensing said substance from said chamber through said outlet.

28. A method for dispensing a substance into a nasal cavity of a user comprising:
providing a nasal inhaler comprising:
a chamber having an interior and an exterior;
a pair of outlets each comprising an exit passageway in flow communication with said interior of said chamber, each of said outlets shaped to be received in a nasal vestibule of the user;
a one-way air inlet valve in one-way flow communication with said interior of said chamber at a first location spaced from said exit passageway; and
a dosage inlet passageway in flow communication with said interior of said chamber at a second location spaced from said exit passageway and from said first location;
providing a container holding said substance, said container comprising a dispensing portion disposed in said dosage inlet passageway;
inserting at least one of said outlets into said nasal vestibule;
dispensing said substance from said container into said chamber; and
dispensing said substance from said chamber through said at least one outlet.

29. A method for dispensing a substance into a nasal cavity of a user comprising:
providing a nasal inhaler comprising:
a chamber having an interior and an exterior;
an outlet comprising an exit passageway in flow communication with said interior of said chamber, said outlet shaped to be received in a first nasal vestibule of the user and wherein said nasal inhaler further comprises a nose plug extending from said exterior of chamber adjacent said outlet;
a one-way air inlet valve in one-way flow communication with said interior of said chamber at a first location spaced from said exit passageway; and
a dosage inlet passageway in flow communication with said interior of said chamber at a second location spaced from said exit passageway and from said first location;
providing a container holding said substance, said container comprising a dispensing portion disposed in said dosage inlet passageway;
inserting said outlet into said first nasal vestibule;
inserting said nose plug into a second nasal vestibule;
dispensing said substance from said container into said chamber; and
dispensing said substance from said chamber through said outlet.

30. The invention of claim 29 wherein said nasal inhaler further comprises a pair of nose plugs positioned on opposite sides of said outlet.

31. A nasal inhaler for introducing a dosage of a substance to a nasal cavity of a user, said nasal inhaler comprising:
a chamber having an interior and an exterior;
an outlet comprising an exit passageway in flow communication with said interior of said chamber, said outlet shaped to be received in a nasal vestibule of the user;
a one-way air inlet valve in one-way flow communication with said interior of said chamber at a first location spaced from said exit passageway, said one-way air inlet valve operative to permit said one-way flow of air from said exterior of said chamber into said interior of said chamber;

an adapter moveably connected with said chamber, said adapter comprising a dosage inlet passageway in flow communication with said interior of said chamber at a second location spaced from said exit passageway and from said first location, said adapter moveable relative to said chamber between a retracted position, wherein at least a portion of said adapter is disposed in said interior of said chamber, and an extended position, wherein at least a portion of said adapter extends from said chamber.

32. The invention of claim 31 wherein a grippable portion of said adapter extends from said chamber when said adapter is in the retracted position.

33. The invention of claim 31 further comprising a container having a dispensing portion and a holding portion, wherein said dispensing portion is disposed in said dosage inlet passageway, and wherein at least a portion of said holding portion is disposed in said interior of said chamber when said adapter is in the retracted position.

34. The invention of claim 31 wherein said adapter is releasably engaged with said chamber when in said retracted and extended positions.

35. The invention of claim 34 further comprising a detent engaged between said chamber and said adapter.

36. The invention of claim 35 wherein said detent comprises a groove formed on said adapter and a first and second rib axially displaced on said interior of said chamber, wherein said first rib is received in said groove when said adapter is in said retracted position and wherein said second rib is received in said groove when said adapter is in said extended position.

37. A method of assembling a nasal inhaler assembly comprising:

providing a chamber having an interior, an exterior, and comprising an intake portion having an intake opening, an outlet comprising an exit passageway in flow communication with said interior of said chamber, said outlet shaped to be received in a nasal vestibule of a user, a one-way air inlet valve in one-way flow communication with said interior of said chamber at a first location spaced from said exit passageway, and an adapter having a dosage inlet passageway and an insert portion;

connecting said insert portion of said adapter with said intake portion of said chamber, wherein said dosage inlet passageway is placed in flow communication with said interior of said chamber through said intake opening at a second location spaced from said air exit passageway and from said first location;

providing a container holding said substance, said container comprising a dispensing portion; and inserting said dispensing portion into said dosage inlet passageway.

38. The invention of claim 37 wherein said connecting comprising inserting said insert portion into said intake opening of said chamber.

39. The invention of claim 38 further comprising releasably engaging said chamber with said adapter using a detent.

40. The invention of claim 38 wherein said adapter comprises a first adapter and further comprising providing a second adapter having a dosage inlet passageway and an insert portion, and wherein said container comprises a first container, and further comprising providing a second container holding a substance, wherein said container comprises a dispensing portion, and further comprising disconnecting said first adapter from said intake portion of said chamber and connecting said insert portion of said second adapter to said intake portion of said chamber, and inserting said dispensing portion of said second container in said dosage inlet passageway of said second adapter.

41. The invention of claim 40 wherein said first container is a nasal spray container and wherein said second container is a pressurized metered dose nasal inhaler.

* * * * *